(12) United States Patent
Cheng et al.

(10) Patent No.: US 11,526,749 B2
(45) Date of Patent: Dec. 13, 2022

(54) METHOD AND SYSTEM FOR ACTIVITY CLASSIFICATION

(71) Applicant: KINETYX SCIENCES INC., Calgary (CA)

(72) Inventors: Chun Hing Cheng, Calgary (CA);
Julia Breanne Everett, Calgary (CA);
Michael Todd Purdy, Calgary (CA);
Travis Michael Stevens, Calgary (CA);
David Allan Viberg, Calgary (CA);
Dale Barry Yee, Calgary (CA)

(73) Assignee: Orpyx Medical Technologies Inc., Calgary (CA)

( * ) Notice: Subject to any disclaimer, the term of this patent is extended or adjusted under 35 U.S.C. 154(b) by 484 days.

(21) Appl. No.: 16/640,765

(22) PCT Filed: Aug. 22, 2018

(86) PCT No.: PCT/CA2018/051011
§ 371 (c)(1),
(2) Date: Feb. 21, 2020

(87) PCT Pub. No.: WO2019/036805
PCT Pub. Date: Feb. 28, 2019

(65) Prior Publication Data
US 2020/0218974 A1 Jul. 9, 2020

Related U.S. Application Data

(60) Provisional application No. 62/548,676, filed on Aug. 22, 2017.

(51) Int. Cl.
*G06N 3/08* (2006.01)
*G06N 3/04* (2006.01)
*A61B 5/00* (2006.01)

(52) U.S. Cl.
CPC .............. *G06N 3/08* (2013.01); *A61B 5/7264* (2013.01); *G06N 3/04* (2013.01)

(58) Field of Classification Search
None
See application file for complete search history.

(56) References Cited

U.S. PATENT DOCUMENTS

| 2011/0054359 | A1 | 3/2011 | Sazonov et al. |
| 2014/0316305 | A1 | 10/2014 | Venkatraman et al. |
| 2019/0001139 | A1* | 1/2019 | Mishra ............... A61N 1/36075 |

OTHER PUBLICATIONS

International Search Reports Written Opinion from PCT/CA2018/051011, dated Nov. 14, 2018.

(Continued)

*Primary Examiner* — Idowu O Osifade
(74) *Attorney, Agent, or Firm* — ATMAC Patent Services Ltd.; Andrew T. MacMillan

(57) ABSTRACT

A method and system for activity classification. A pressure sensor receives input data resulting from physical activity of a subject performing an activity. The input data includes pressure data from at least one pressure sensor, and may include other data acquired through other types of sensors. A deep learning neural network is applied to the input data for identifying the activity. The neural network is trained with reference to training data from a training database. The training data may include empirical data from a database of previous data of corresponding activities, synthesized data prepared from the empirical data or simulated data. The training data may include data from physical activity of the subject being monitored by the system. Different aspects of the neural network may be trained with reference to the training data, and some aspects may be locked or opened depending on the application and the circumstances.

20 Claims, 12 Drawing Sheets

(56) References Cited

OTHER PUBLICATIONS

Jones, An Introduction to Neural Networks, (20041200), URL: https://www.roguewave.com/sites/rw/files/attachments/NeuralNetworkWP1.pdf?sitename=RogueWave.

Uhrig, "Introduction to Artificial Neural Networks", Proceedings of IECON '95—21st Annual Conference on IEEE Industrial Electronics, doi:doi:10.1109/IECON.1995.483329, (Nov. 10, 1995), pp. 33-37, URL: https://ieeexplore.ieee.ore/document/483329, XP010154773.

* cited by examiner

METHOD AND SYSTEM FOR ACTIVITY CLASSIFICATION

CROSS-REFERENCE TO RELATED APPLICATIONS

This application is a national stage entry of International Patent Application No. PCT/CA2018/051011 filed on Aug. 22, 2018 and entitled "METHOD AND SYSTEM FOR ACTIVITY CLASSIFICATION", which claims the benefit of priority of U.S. Provisional Patent Application No. 62/548,676 filed Aug. 22, 2017 and entitled "METHOD AND SYSTEM FOR ACTIVITY CLASSIFICATION", both of which are incorporated herein by reference in their entirety.

FIELD

The present disclosure relates to classification of physical activities.

BACKGROUND

Monitoring and quantifying physical activity facilitates effective exercise and healthy living. Devices that count steps and log exercise are increasingly common as people increasingly take ownership of and interest in their own well-being. Similarly, careful monitoring of activity on the worksite can be important in preventing workplace-related injuries. However, even with the most precise of these available devices, distinguishing between certain types of activity can be very difficult.

Commonly used devices apply inertial data, primarily from accelerometers and gyroscopes, to determine activity type, though several technologies also include pressure sensing and acoustic measurement systems. Activity type is then classified by comparing data collected from one or more of these sensors to predetermined, pre-programmed characteristics of a number of common activities. However, these systems are limited in their ability to distinguish between unique occurrences of similar activities, to classify transition stages between definitive activity types, or to account for personal attributes of the subject being monitored.

There is call for improved approaches to classification of physical activities that can distinguish between potentially small measurable differences between activities, and accurately classify physical activities.

SUMMARY

Herein provided are a system and method for classifying physical activity of a subject. Input data including pressure data is collected from sensors during activities performed by the subject. The input data may also include other types of data. A deep learning neural network ("NN") is applied to the input data, providing classified activity data defining the activities. Weights and biases define relationships between consecutive layers within the NN. The weights and biases may be initially set and updated by supervised training to account for specific attributes of the subject, facilitating activity classification for the subject specifically. The supervised training may include population training based on training data from a training database, which may be used in a network training scenario. The supervised training may include personalized subject training based on input data from an individual. The individual may be the subject or an individual other than the subject. Input data used in training may be from a previously recorded activity session and applied to training using batch processing, which may facilitate training of the system prior to use. Once use has begun, the input data may be streamed directly from the sensor module, requiring online or near-real-time processing. The real-time training or activity classification may be applied after training of the system. Certain layers and nodal relationships within the NN may be locked after calibration by the training data, and other layers and nodal relationships updated with ongoing training.

The NN may apply activity classification across an entire data set of the input data. The NN may apply activity classification across a specified window of time of the input data. The window of time may be the known and static width of an event identified by a user, who may be the subject or a different individual, within the input data, in which the event is a distinct waveform within the input data and delineated using known event detection methods. The window of time may be of a defined time range that is progressed through the input data and the input data within the time window is classified before translating the time window along a timeline of the input data to apply the NN to a subsequent portion of the input data within the time window after translation. The time window may be weighted, such that it has a weighted segment in which data within that segment are given a weighted preference when the NN is applied to classification of the activity within the bounds of the weighted time window. The input data may also be classified through an event window in which an event is detected in the input data, event limits defined on either side of the event, and then the input data within the event window may be classified. The classified activity data may be communicated to a user by display of the classified activity or by storage of the classified activity data. The user may be the subject or an individual who is not the subject. The subject may be the user, an individual who is not the user, a prosthetic limb used by an individual, an animal, an autonomous vehicle, a robot, or any suitable subject that may apply pressure to a surface during activity.

The pressure data may be collected from pressure sensors located on the body of the subject. Pressure sensors may be placed on the plantar portion of the foot to measure plantar pressure during physical activity. Sensors for other types of input data indicative of a physical activity may also be used in the system. The input data may also be collected from a variety of sensors, including accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, drug level sensor, or any other type of sensor that measures the level of impairment, or any other sensor that receives the input data.

The NN may be a neural network with translational invariance. The NN may be a convolutional neural network ("CNN"). The CNN includes at least one convolutional layer and at least one fully connected layer. The NN may comprise long short-term memory ("LSTM") units. The NN may be a combination of neural network types, for example, using a CNN to model relationships between spatial components of the system, such as different sensors, and using an LSTM system to model temporal components of the system, such as data points in time.

Population training includes providing population training data to the NN. The population training data includes pressure data and may include other input data acquired from a variety of subjects with varying physical attributes and performing one or more defined activities. The variety of subjects makes up a population. Input data resulting from each of the subjects in the population performing the defined activities makes up a training database. The training database may include empirical input data or synthetic input data generated from pressure data or other input data. The NN classifies activities based on the population training data to provide classified training data. The classifications may be in the form of probabilities of likelihood that a given estimated activity is the actual activity. The classifications may be expressed as the likelihood that a given portion of the classified activity data corresponds to is the actual activity. The actual activities and the corresponding classified actual activity data are known. The classified actual activity data are the known classification of the actual activities. The classified actual activity data is provided through a training confirmation and the classified actual activity data is compared with the classified training data. The NN may be updated according to a loss function defined as the measure of discrepancy between the classified training data and the classified actual activity data by adjusting the weights and biases to mitigate the loss function. The measure of discrepancy may be the difference, the squared difference, cross-entropy, or another measure of discrepancy between data sets. Population training data including a variety of activities performed by a variety of subjects may be accessed from the training database. The NN may be applied to the population training data and the weights and biases updated based on the classified activity data resulting from applying the NN to the training database. Stored classified activity data may be combined with the population training data and included in the training database for facilitating population training for the subject and for other subjects who access the training database. The population training may be applied initially to optimize the weights and biases before use, and may be repeated thereafter, including by receiving updated training data periodically or sporadically.

Subject training may be applied to train the NN with reference to subject training data. The subject training data may include input data resulting from the subject performing one or more defined activities. The NN classifies the defined activity based on the pressure data to provide the classified activity data. The classifications may be expressed as a probability that the classified activity data corresponds to the actual activity. The defined activity is known and the corresponding classified actual activity data that is expected to result from application of the NN to the pressure data associated with the defined activity are known. The classified actual activity data is compared with the classified activity data. The NN may be updated according to a loss function defined between the classified activity data and the classified actual activity data by adjusting the weights and biases to mitigate the loss function. The subject's specific attributes direct the resulting input data, and as a result, the subject training is based on data that is inherently specific to the subject. Subject training may be applied in association with a confirmation input that provides the classified actual activity data. Subject training may be applied following a prompt to the subject to perform the defined activity. Subject training may be a specific routine that the NN applies in response to a user input, or may be available during the ordinary course of activity classification in response to the confirmation input or following the prompt.

The subject training data may be used to train the NN after it has already be trained by the training database. Once the NN has been trained by the training database, providing the population-trained NN, the weights and biases of multiple layers of the NN are defined. The weights and biases within all or a subset of the layers of the NN may be locked, such that the subject training data cannot change the weights and biases. Administration of the subject training data to the population-trained NN results in loss functions when compared to the classified actual activity data corresponding to the subject training data. The NN may be updated according to the loss function by adjusting the weights and biases that are not locked to minimize the loss function, or the system loss function. Subject training may be applied to adjust the weights and biases that are not locked within the NN, providing the personalized NN that is based on a population-trained NN. The weights and biases that are not locked may be within subsequent layers of the NN that are downstream of an initial input layer. For example, subject training of a CNN may adjust the weights and biases within a fully connected layer and a pre-classification layer, while convolutional layers may be locked during population training.

Processing of the classified activity data through the NN, the population training or the subject training may be applied after inputting user data with an input module. The user data may define specific attributes of the subject and otherwise relate to the subject. Where the subject is an individual, user data may include personal attributes of the subject (e.g. age, sex, weight, height, shoe size, physical conditions, mental conditions, limb length, body fat index, location, elevation, limb position, number of hours awake, or any attributes that relate to the user, etc.). The user data may be applied to selecting initial weights and biases, or updating the weights and biases, based on the training database or the subject training data. Where a CNN is used, the user data may be concatenated into the fully connected layer for classifying the convoluted and pooled input data. In an NN other than a CNN, the user data may be input into one of the layers of the NN. Population training or subject training may facilitate application of the NN for classifying activity performed by the subject over a session of a few seconds by taking into account specific attributes of the subject from the user data. If the subject changes activities during the session, the NN may classify multiple activities types performed during the session. The NN may classify transitions from one activity type to the next, and between separate occurrences of one activity type.

Processing of the input data through the NN may be in real-time during collection of data, or in a batch after data has been collected. A time window defining a time range may be applied to the input data and the NN applied to the input data within the time window. The NN may be applied to the input data corresponding to the time points within the time window and the input data classified, providing classified activity data. The time window is then progressed along a timeline of the input data by a defined amount, and the data within that window is inputted to the NN and classified, providing a rolling account of estimations of the activities performed during acquisition of the input data. The input data within each time window may be weighted such that a scaling value that increases the importance of a portion of the input data within the time window.

Processing of the input data through the NN may be done for only specific sections of the input data that have been identified using a known event detection method. The event detection method may delineate distinct events within the data set, and the data within the delineated event may be input into the NN and classified, providing classified activity data.

The classified activity data may be presented as a composition of estimated activities, such that the classified activity data is presented as a percentage breakdown of a variety of activities. The highest percentage activity from within the composition of estimated activities represents the activity that the NN has identified. The composition of estimated activities may represent a transition between activities. For example, the NN may classify the activity with an 80% chance of being walking, and 20% chance of being running, which may represent a transition between walking and running.

The activity classification system may be applied to measurement of pressure on the soles of a subject to classify activities that involve gait, steps and other activities that result in pressure on the soles of the subject. The activity classification system may be applied to measurement of pressure and blood glucose levels in cascade to correlate activity levels with blood glucose, and in some cases to deliver insulin in response to blood glucose levels. Similarly, indicators for the need to administer drugs, therapeutics or other substances based on the classified activity data may be leveraged to prompt the subject or a caregiver to provide the substance, or the indicators may trigger an automatic delivery system. The activity classification system may be applied to fall prediction by measurement of pressure on soles to predict an imminent fall and warn the subject. Systems directed to fall detection may also contact caregivers if a fall is detected, and may include inertial sensors to facilitate characterizing aspects of gait relevant to slipping and falling. Such systems may alert the subject through tactile or other intuitive feedback that allows an instinctive response to the feedback. Similarly, the system may be applied to prompting users In a first aspect, herein provided is a method and system for activity classification. A pressure sensor receives input data resulting from physical activity of a subject performing an activity. The input data includes pressure data from at least one pressure sensor, and may include other data acquired through other types of sensors. A deep learning neural network is applied to the input data for identifying the activity. The neural network is trained with reference to training data from a training database. The training data may include empirical data from a database of previous data of corresponding activities, synthesized data prepared from the empirical data or simulated data. The training data may include data from physical activity of the subject being monitored by the system. Different aspects of the neural network may be trained with reference to the training data, and some aspects may be locked or opened depending on the application and the circumstances.

In a further aspect, herein provided is a method for classifying an activity of a subject comprising: receiving input data of the subject resulting from the activity, the input data including pressure data; applying a deep learning neural network to the input data based on weights and biases, resulting in classified activity data; training the deep learning neural network for updating the weights and biases; and communicating the classified activity data to a user.

In some embodiments, the input data comprises binary inputs of data above or below a threshold value of the input data.

In some embodiments, the input data comprises quantitative inputs of a pressure magnitude detected by a pressure sensor.

In some embodiments, the input data comprises additional data.

In some embodiments, the additional data comprises data from an accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, or drug level sensor.

In some embodiments, the weights and biases are initially determined with reference to relationships between separate sources of the input data.

In some embodiments, the separate sources of the input data comprise separate sensors on a support matrix located to receive the input data from different portions of the subject; and the weights and biases are initially determined with reference to the locations of the separate sensors on the support matrix.

In some embodiments, training the deep learning neural network comprises: confirming the activity, resulting in a defined activity and corresponding classified actual activity data; defining a loss function between the classified actual activity data and the classified activity data; and updating the weights and biases for mitigating the loss function.

In some embodiments, confirming the activity comprises prompting the subject to perform the defined activity.

In some embodiments, confirming the activity comprises receiving a confirmation input that the subject performed the defined activity.

In some embodiments, receiving the confirmation input comprises receiving the confirmation input from the subject.

In some embodiments, receiving the confirmation input comprises receiving the confirmation input from an individual other than the subject.

In some embodiments, the deep learning neural network comprises a translationally invariant neural network.

In some embodiments, the translationally invariant neural network comprises: at least one convolutional layer; and at least one fully connected layer subsequent to the at least one convolutional layer.

In some embodiments, the method includes receiving user data of attributes of the subject; and wherein the fully-connected layer comprises the user data concatenated with the fully-connected layer.

In some embodiments, the translationally invariant neural network comprises a long short-term memory system.

In some embodiments, training the deep learning neural network comprises: receiving training data of at least one reference subject performing a defined activity from a training database; applying the deep learning neural network to the training data based on the weights and biases, resulting in classified training data; receiving classified actual activity data from the training database; defining a loss function between the classified training data and the classified actual activity data; and updating the weights and biases for mitigating the loss function.

In some embodiments, the training data comprises empirical input data.

In some embodiments, the training data comprises synthetic input data generated from the empirical input data.

In some embodiments, the synthetic input data is generated from the empirical input data by applying to the empirical input data one or many of the following operations: time-shifting, magnitude-scaling and spectral magnitude-scaling.

In some embodiments, the reference subject is the subject.

In some embodiments, the method includes receiving a confirmation input that the subject performed the defined activity and wherein the empirical input data comprises input data confirmed to correspond to the defined activity by the confirmation input.

In some embodiments, the empirical input data comprises input data received following a prompt to the subject to perform the defined activity.

In some embodiments, the reference subject comprises an individual selected with reference to attributes of the subject.

In some embodiments, the reference subject comprises a plurality of individuals.

In some embodiments, the training data comprises data of the plurality of individuals performing the defined activity, and at least a portion of the plurality of individuals performing at least one activity other than the defined activity.

In some embodiments, training the deep learning neural network comprises: initial training based on first relationships between a first group of layers of the deep learning neural network; locking the first relationships; and subsequent training based on second relationships between a second group of layers of the deep learning neural network.

In some embodiments, the initial training is based on training data in a training database.

In some embodiments, the subsequent training is based on updated training data received from the training database.

In some embodiments, the subsequent training is based on empirical data of the subject.

In some embodiments, communicating the classified activity data to the user comprises displaying the classified activity data, providing tactile stimulus to the subject, or storing the classified activity in a database.

In some embodiments, the activity comprises activity indicative of an imminent fall and communicating the classified activity data to the user comprises a tactile or other neuroplastic stimulus to prompt the user to correct the activity and avoid a fall.

In some embodiments, the activity comprises activity indicative of an imminent fall and communicating the classified activity data to the user comprises a tactile or other neuroplastic stimulus to prompt the user to correct the activity and avoid a fall.

In some embodiments, the activity further comprises a fall and further comprising communicating the classified activity data of the fall to a third party.

In some embodiments, the method includes applying a time window to the input data to provide time-segmented input data; and wherein applying the deep learning neural network to the input data comprises applying the deep learning neural network to the time-segmented input data.

In some embodiments, the method includes weighting the time-segmented input data to provide weighted input data and wherein applying the deep learning neural network to the input data comprises applying the deep learning neural network to the weighted input data.

In some embodiments, applying an event detection filter to the input data to event-classified input data; and wherein applying the deep learning neural network to the input data comprises applying the deep learning neural network to the event-classified input data.

In some embodiments, the method includes receiving user data of attributes of the subject.

In some embodiments, the user data includes medical data of the subject.

In some embodiments, the weights and biases are updated with reference to the user data.

In some embodiments, the method includes receiving metabolic load data; applying the classified activity data and the metabolic load data to a metabolic load neural network, providing classified combined metabolic and activity data; and communicating the classified combined metabolic and activity data to the user.

In some embodiments, the method includes administering a substance to the subject in response to the classified combined metabolic and activity data.

In some embodiments, the method includes applying the classified activity data to a second deep learning neural network, resulting in second classified activity data.

In some embodiments, the method includes receiving second input data, and wherein applying the classified activity data to a second deep learning neural network comprises applying the second input data and the classified activity data to the second deep learning neural network.

In some embodiments, the activity includes standing, sitting, lying, crouching, walking, running, shuffling, skipping, dancing, ascending or descending stairs, a ramp or a ladder, cycling, situps, crunches, pushups, skiing, snowboarding, lifting weights, deadlift, lunges, jumping jacks, squats, mountain climbers, bench dips, step ups, planking, calf raises, burpees, growing, shoulder press, bicep curls, tricep dips, speed-walking, skateboarding, bowling, driving, tapping feet or otherwise fidgeting, or other steps or footfalls of the subject, which may change speed, pace, or direction.

In a further aspect, herein provided is a system for classifying activity of a subject comprising: a sensor module comprising a pressure sensor for receiving input data during the activity, the input data including pressure data; a processor configured for receiving the input data, the processor configured for executing a method comprising: applying a deep learning neural network to the input data based on weights and biases, resulting in classified activity data; and training the neural network for updating the weights and biases.

In some embodiments, the sensor module comprises at least two pressure sensors; and the weights and biases are biased based on known relationships between the at least two pressure sensors.

In some embodiments, the input data comprises additional data.

In some embodiments, the sensor module comprises an accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, drug level sensor, or any other type of sensor that measures the level of impairment for receiving the additional data.

In some embodiments, the sensor module comprises a sensor for receiving a magnitude of input data.

In some embodiments, the sensor module comprises a sensor for receiving an indication of whether a threshold of the input data has been exceeded.

In some embodiments, the deep learning neural network comprises a translationally invariant neural network.

In some embodiments, the neural network comprises: at least one convolutional layer; and at least one fully-connected layer subsequent to the at least one convolutional layer.

In some embodiments, the fully-connected layer comprises user data concatenated with the fully-connected layer.

In some embodiments, applying a deep learning neural network to the input data comprises applying a time window to the input data to provide time-segmented input data; and applying the deep learning neural network to the time-segmented input data.

In some embodiments, the system includes weighting the time-segmented input data to provide weighted input data and wherein applying the deep learning neural network to the input data comprises applying the deep learning neural network to the weighted input data.

In some embodiments, applying a deep learning neural network to the input data comprises applying an event detection filter to the input data to event-classified input data; and applying the deep learning neural network to the event-classified input data.

In some embodiments, training the deep learning neural network comprises: confirming the activity, resulting in a defined activity and corresponding classified actual activity data; defining a loss function between the classified actual activity data and the classified activity data; and updating the weights and biases for mitigating the loss function.

In some embodiments, the training data comprises synthetic input data generated from empirical input data.

In some embodiments, training the deep learning neural network comprises initial training based on first relationships between a first group of layers of the deep learning neural network; locking the first relationships; and subsequent training based on second relationships between a second group of layers of the deep learning neural network.

In some embodiments, the system applies any of the embodiment of the method described herein.

In some embodiments, the activity includes standing, sitting, lying, crouching, walking, running, shuffling, skipping, dancing, ascending or descending stairs, a ramp or a ladder, cycling, situps, crunches, pushups, skiing, snowboarding, lifting weights, deadlift, lunges, jumping jacks, squats, mountain climbers, bench dips, step ups, planking, calf raises, burpees, growing, shoulder press, bicep curls, tricep dips, speed-walking, skateboarding, bowling, driving, tapping feet or otherwise fidgeting, or other steps or footfalls of the subject, which may change speed, pace, or direction.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures, in which reference numerals having a common final two digits refer to corresponding features across figures (e.g. the system 10, 110, 210, 310, 410, 510, 610, 710, etc.).

DETAILED DESCRIPTION

Figure 1:
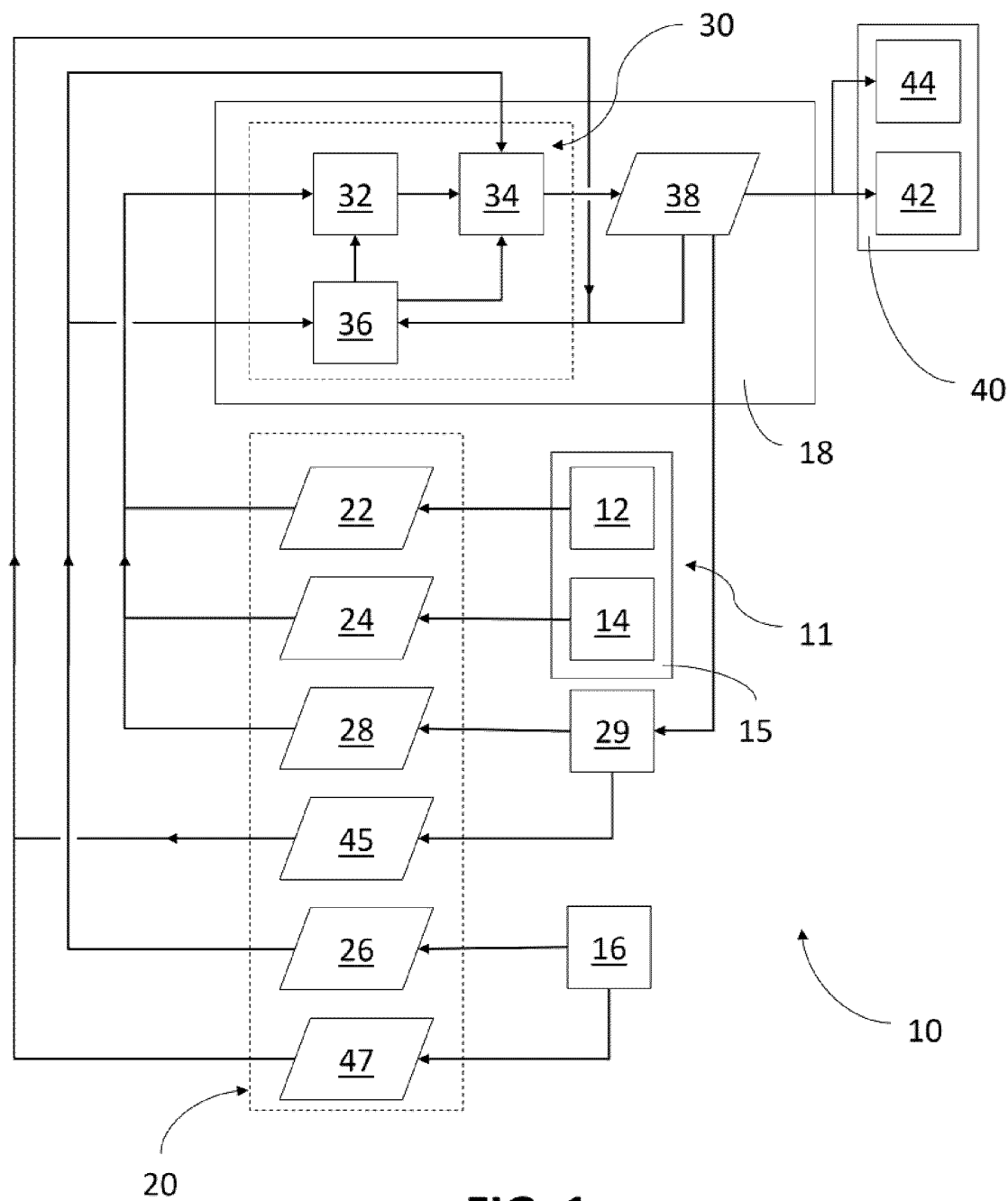
FIG. 1 is a block diagram illustrating selected hardware and process components of an activity classification system using a CNN.

Herein provided are a system and method for classifying physical activity of a subject based on input data resulting from the subject's physical activity. The input data includes pressure data collected from sensors during activities performed by the subject. Additional sensors may be applied to provide other types of data to complement the pressure data (e.g. an accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, drug level sensor, or any other type of sensor that measures the level of impairment, etc.). The subject may be an individual, a prosthetic limb used by an individual, an animal, an autonomous vehicle, a robot, or any suitable subject that may apply pressure to a surface during activity.

A deep learning neural network ("NN") is applied to input data including the pressure data and any additional types of data, providing classified activity data defining the activities of the subject. The NN includes layers made of nodes. Weights and biases define relationships between the nodes of an NN. The NN may include a convolutional neural network ("CNN"), a long short-term memory ("LSTM") system, or any other NN that incorporates translational invariance. The NN is a deep learning artificial intelligence engine. Where a CNN is applied, the CNN includes at least one convolutional layer and at least one fully connected layer. Known relationships between inputs of input data are used to define weights and biases connecting nodes in consecutive layers within the NN to one another. The NN classifies activities based on inputs of the input data according to weights and biases in each layer. The weights and biases may be initially defined with reference to random values within a defined range, previous data in a training database, user inputs to the NN, the relationships between input data points from separate moments in time. The weights and biases may be initially defined by relationships between nodes, and may be related in a variety of ways. The nodes that represent different sensors in space may be related to one another for an instant in time. For example, pressure sensors on heels of each of a pair of may be instantiated as negatively correlated, whereas two toe sensors on the same foot might have positive correlation. In another example, nodes that represent different time points for one sensor may have relationships for nodes that are close in time, such as a correlation between a current value and a value read 10 milliseconds ago, in which case a high reading may climb then fade rather than jumping instantaneously from low to high. Definition of nodes being close in space or in time would be driven by the particular use case.

The weights and biases may be updated by supervised training of the NN based on population training. The weights and biases may be updated by supervised training of the NN based on subject training to recognize the specific attributes of the subject, facilitating activity classification for the subject specifically. The supervised training may include subject training based on the input data or population training based on training data from a training database.

The training data may be empirical data, synthetic data based on empirical data or simulated data. The classified activity data may be communicated to a user by displaying or storing the classified activity data. The user may be the subject or an individual who is not the subject. The training database may be built from training data from one or more subjects, one or more experts, or combinations thereof. The training database may serve as a coaching tool to classify the subject's activities to the subject's past activities. The training database may serve as a coaching tool to classify the subject's activities in relation to an expert or to a set of users.

In the NN, the input data may be plotted as a two-dimensional matrix. The matrix represents a window subset of pressure data from each pressure sensor, any sources of sensor data other than pressure data, any manual input from the user, and any other sources of the input data. The matrix may be represented as rows and columns. Each pressure sensor or other source of the input data may be represented as a column of data. Each row may be represented as a moment in time, with data extending along a column representing data from one sensor or other source of data acquired over time. Each cell corresponds to a data node. Connections between nodes in convolutional layers may define patterns in the overall data series. The connections defined between nodes provide the basis for the NN to define and identify activities. The more developed the connections between nodes, the greater degree to which the NN may facilitate activity classification.

Connections may be made between nodes in the pressure data matrix and nodes in a feature map of a subsequent convolutional layer. Connections may be made between nodes in feature maps of adjacent convolutional layers. Connections may be made between nodes of feature map of a convolutional layer and a fully-connected layer. Connections between nodes may be forgone if it is determined that there is no relationship between the points Connections may be made between nodes in the pressure data matrix and a feature map of a convolutional layer based on data in the pressure data matrix from a selected pressure sensor or other source of the input data across a span of time (i.e. along columns in the two-dimensional matrix). Connections may be made between nodes in the pressure data matrix and a feature map of a convolutional layer based on data in the pressure data matrix from different pressure sensors or other sources of the input data that represent data from different pressure sensors or other sources of the input data in a single moment in time (i.e. along rows in the two-dimensional matrix).

A pressure sensor or other sources of input data may provide the input data in predictable patterns according to the activity being performed by the user. Where patterns in the input data from a pressure sensor or other sources of input are known, minimally correlated patterns are given low values, highly correlated patterns are given large positive values, and negatively correlated patterns are given large negative values.

Separate pressure sensors or other sources of input data may have predictable relationships with one another according to the activity being performed by the user. Where relationships between pressure sensors, or between pressure sensors and other sources of input are known, relationships between minimally correlated pressure sensors or other sources of input are given low values, relationships between highly correlated pressure sensors or other sources of input are given large positive values, and relationships between negatively correlated pressure sensors or other sources of input are given large negative values.

The method and system may be applied to activity classification of a subject undertaking a variety of physical activities (e.g. standing, sitting, lying, crouching, walking, running, shuffling, skipping, dancing, ascending or descending stairs, a ramp or a ladder, cycling, situps, crunches, pushups, skiing, snowboarding, lifting weights, deadlift, lunges, jumping jacks, squats, mountain climbers, bench dips, step ups, planking, calf raises, burpees, growing, shoulder press, bicep curls, tricep dips, speed-walking, skateboarding, bowling, driving, tapping feet or otherwise fidgeting, or other steps or footfalls of the subject, which may change speed, pace, or direction, etc.). In such cases, heel pressure sensors on either foot may expect to have a negative correlation to one another during walking, as the heel of one foot is in the swing phase while the other is striking the ground, or in the stance phase. Conversely, the toes of the foot exert high and low pressures at similar times, and so sensors near these toes are positively correlated. Also in such cases, as the subject takes a slow step over about five seconds, in the first two to three seconds, readings on a heel may have a similar amount of pressure as at the start of the step. Later in the step cycle, the amount of pressure on the heel may be less than at the start of the step. Characterizing step data in this manner may be facilitated by pressure sensors that measure an amount of pressure. Other pressure sensors may sense only whether a preselected pressure threshold has been exceeded, which may conserve bandwidth compared with receiving data of an amount of pressure.

Connections between nodes are made through functions specific to each nodal connection relationship. The activity classification process begins with the data matrix of the input data being divided into subsets of a defined time window duration. Weights and biases are set based on any known correlations, which may be from the training database including previous empirical data, simulated data, and synthesized data based on empirical data. Each time window of the input data is passed through the NN. The time window may be a time window, in which a window of defined time duration is progressed across the data matrix. Only data constrained by the time bounds of the time window has the NN applied to it. After application of the NN, and subsequent classification, the time window is progressed along the time axis of the input data, and the input data confined within the new time-bounds of the time window is subjected to the NN.

The time window may apply a weighting to a portion of the input data within the time window. Weighting of the input data will highlight a portion of the input data within the time window. A known and previously applied event detection method may define an event window. Such an event detection method may identify events of interest within the input data, for example, a step within a walking session. The event window is then be defined as the input data within the bounds of the event window that the event detection method delineates. The event window subset of data is the subjected to the NN, and the input data within the event window is classified.

The NN includes multiple layers. Where a CNN is applied, the CNN includes at least one convolutional layer and one fully-connected layer. Each convolutional layer includes a convolutional step in which one or more filter masks are applied to each of one or more feature maps having activation functions for establishing connections with nodes in a subsequent layer, and a pooling step. The filter masks may be updated as the masks are applied to different portions of the data matrix to differently account for the pressure data depending on the portion of the data matrix to which the filter mask is applied. The filter masks may also be updated in the convolutional layers depending on the portion of a feature map to which the filter mask is applied.

Connections between nodes in adjacent layers may be as described in Eq. 1.

$$y_j^k = \max_{l \in C_j} \left\{ f\left( \left( \sum_{h=0}^{M} \sum_{i \in D_l} w_{il}^{hk} x_i \right) + b_j^k \right) \right\} \quad \text{(Eq. 1)}$$

In Eq. 1, a connection between a value $x_i$ at node i to a value $y_j^k$ at a related node j is established. Node i is in a first layer and node j is in an adjacent second layer, with index k for the feature maps of the adjacent second layer. The first layer may be an input data matrix or convolutional layer. The second layer may be a convolutional layer or a fully connected layer.

The value $x_i$, is multiplied by the weight, $w_{il}^{hk}$, of the corresponding relationship between the related nodes i and j. Related nodes are included in subset $D_l$. Subset $D_l$ represents nodes that are spatially close, logically close or temporally close. Sensors that are logically close may include sensors that have an expected relationship or correlation to one another. These products are summed together. The summation of the products, and inclusion of only a defined subset of values represents the convolution process.

This process is performed a number of times in order to increase the robustness of the system. Each nodal connection between has its own weights and biases. There are M feature maps in this layer, indexed by h. A bias $b_j^k$, specific to the relationship between each node, is added to the summation. Where the first layer is an input data layer, there are M data matrices in the input layer.

The calculated summations are applied in a pre-determined activation function f. The rectified linear unit function relu(x) may be the activation function between convolutional layers. The results are pooled to reduce the number of nodes that pass from the first layer to the second layer. One approach to pooling is maximum pooling, as in Eq. 1. In maximum pooling, the largest node within a subset $C_j$ is the only value to pass through to the next layer. The convolution steps and pooling steps are performed in each convolutional layer.

The convolution step and the pooling step may be applied to the matrix of the input data or to a feature map of the convoluted data using a filter mask that accounts for data from one sensor over time. When applied to the input data, the convolution and pooling steps may associate time nodes corresponding to the same sensor at different points in time, and which are temporally close to one another, such as within a predetermined timespan before and after the instance represented by the node. When applied to the input data, the convolution step and the pooling step may associate nodes corresponding to multiple sensors at a single moment in time. The associations may result in weights and biases that correspond to positive, negative, or non-existent correlations between sensor data.

The filter masks may also be updated for different portions of a data matrix or feature map to which the filter masks are applied. In some cases, a filter mask may apply non-zero values to time points for a first sensor, but at a first selected certain time point, apply non-zero values to a first group of related sensors at the first selected time point. Similarly, the filter mask may apply non-zero values to a second group of related sensors at a second selected time point. In such cases, the filters may assign a non-zero value to all time data in each sensor, and at certain time points for each sensor, assign a non-zero value to other sensors' readings at the certain time points.

After processing in the convolutional layers, the values are processed through one or more fully connected layers to provide classified activity data. As the name may suggest, nodes in fully connected layers are connected to every other node in subsequent layers. No convolution or pooling steps are employed. An example of a function for a fully connected layer is shown in Eq. 2:

$$y_j = g\left( \left( \sum_{i=1}^{N} w_{ij} x_i \right) + b_j \right) \quad \text{Eq. 2}$$

In the fully connected layers, the values $x_i$ and $y_i$ of connected nodes i and j are similarly subject to weights and biases. The weight $w_{ij}$ is multiplied by the value of $x_i$, the products are similarly summed together and added to a bias $b_j$, and this value is placed through another activation function f. The hyperbolic tangent function may be used as an activation function for the fully connected layers.

The data set in a fully connected layer is a one-dimensional vector rather than a two-dimensional matrix as in the convolutional layers. Additional data, such as specific attributes of the subject, may be concatenated to the vector of the first fully connected layer. The input data following the convolutional layers and the concatenated data are passed through the first fully connected layer and any subsequent fully connected layers. The output from the final fully connected layer is classified activity data.

The classified activity data may be presented as a set of percentages that represent the likelihood that the activity matches each of a set of possible activities. For example, the system may record a long session where a subject engages in several activity types. The resulting classified activity data for a given subset of the input data within the session may describe an estimation that the activity has a high likelihood of being walking. The classified activity data for a second given subset of the data may describe a high likelihood that the input data in that subset describes running. Transitions between activities may be characterized as a combination of two activities, with likelihoods of being one or the other. A person switching from walking to sprinting may have a transition period where a window reports an output score comprised partially of walking and partially of running. Transitions between phases are classified into classified activity data that include non-binary outputs, with the non-binary outputs defining a ratio of one activity to another activity in the classified activity data (e.g. jogging could be classified as partially running and partially walking, skipping could be classified as partially running and partially jumping, etc.).

Initially, the weights and biases between each node are set randomly or according to previously-characterized activity. The weights and biases for a given nodal relationship may be assigned values within a range that corresponds to the anticipated relationships between nodes. In one example, pressure sensors on opposite heels may have a negative correlation with one another for characterizing a walking activity, and as such, the random weight and bias values may be centered around a normalized large negative number in order to ensure a closer fit to a negative correlation when training the NN. These weights are not definite, so if these assumptions made regarding the sensor relationships prove to be incorrect, the NN will resolve the assumption. Setting the weights and biases arbitrarily will allow the NN to define these parameters on its own without applying any assumptions.

Supervised Training of the NN includes a forward step and a backpropagation step. For a CNN, in the forward step, data is propagated through the convolutional layers (Eq. 1) and fully connected layers (Eq. 2) to classify the data into activities, providing predicted activity data. A similar approach is taken for a NN other than a CNN with respect to the layers of the NN. The predicted activity data is compared to control activity data, and the difference between the two is defined as loss function. The loss function may be the difference, the squared difference or the cross entropy between the predicted activity data and the control activity data. The backpropagation step then uses this error to adjust the weights and biases. The adjustments are computed using the gradients of the values and the weights and biases, through the inverse of the activation function related to the index of the node from which the pooling step (e.g. maximum values, minimum values, mean values, etc.) was taken. Dropout, noise, or other regularization techniques may be used to prevent overfitting the experimental data. A derivative at each node may be applied to a loss function to minimize the loss function and define adjustments to the weights and biases to mitigate the error and train the NN. The control activity data may be provided from a confirmation input that the subject completed a defined activity or from a training confirmation received from a training database including data of known activities.

A system may be individualized to a specific subject by highlighting input data collected from that subject in a subject training process. Subject training includes providing the input data to the NN while the subject performs a defined activity and providing the confirmation input to the NN that the defined activity has been performed. The NN classifies activities based on the input data to provide the classified activity data. The defined activity is known and the corresponding classified actual activity data that is the expected classification result from application of the NN to the input data associated with the defined activity is known. The classified actual activity data is compared with the classified activity data. The NN may be updated according to a loss function defined between the classified activity data and the classified actual activity data by adjusting the weights and biases to minimize the loss function. The subject's specific attributes direct the input data, and as a result, subject training is based on data that is inherently specific to the subject. Subject training may be applied following a prompt to the subject to perform the defined activity or during the ordinary course of activity classification. The confirmation input may be from a user verifying that the subject performed or is about to perform the defined activity. When combined with population training, classified activity data from subject training may be weighted and biased accordingly and added to the training database.

Subject training may be used in combination with population training to train a NN. The weights and biases within a subset of layers of the NN may be locked following population training, leaving only a separate subset of weights and biases open to change during further training. During subsequent subject training, only the weights and biases within those layers that are not locked may be modified according to the loss function.

Population training includes providing the training data to the NN. The training data may include pressure data and other input data acquired from a variety of subjects with varying specific attributes, performing a variety of known activities. The NN classifies activities based on the training data to provide classified training data. The actual activities and the corresponding classified actual activity data are known. The classified actual activity data is compared with the classified training data. The NN may be updated according to a loss function defined between the classified training data and the classified actual activity data by adjusting the weights and biases to minimize the loss function. Stored classified activity data may be combined with the training data and included in the training database for facilitating population training for other subjects. Training the system with the training data may facilitate application of the NN to classify activity for a new subject.

The training database may include empirical data and synthesized data. Empirical data may be acquired from a diverse variety of subjects performing a diverse variety of activities. To reduce the number of actual subjects needed to train the system, synthesized data may be created by randomly varying the empirical data. Varying the data series to provide synthesized data may be through random time shifting, random magnitude scaling, random pattern changing or other approaches to varying a dataset. Random time shifting uses a smoothed series of random time translations applied to each time data point in a data set. Random magnitude scaling works similarly, whereby a smoothed scaling value is applied to each sensor data point. Random pattern changing is accomplished by making minor perturbations to the spectral amplitudes of the data set. These perturbations may be made globally to the entire data series (e.g. with a Fourier Transform, etc.), or locally (e.g. with the S-Transform, etc.). Other approaches to synthesizing data from empirical data may include making minor smoothing adjustments to the time-axis, magnitude, and local and global frequency spectrum such that said synthesized values simulate variations in performance of activities of the same type. Use of synthesized data may mitigate overfitting of the NN by non-diversified training data.

The synthesized training data may facilitate preparing a system for use in characterizing activities of a given subject with less empirical data. Deep learning networks typically rely on a large training database to train initial weights and biases of the NN. Application of synthesized training data may reduce the number of subject training sessions based on the confirmation input required before using the system for characterizing activity of a given subject. The synthesized data can balance the training data to introduce diversity, such that the distribution of activity data is less biased toward the aggregate trends of the particular individuals in the database. In some cases, the training database may display trends that are not representative for the subject or for a broader population than that in the training database (e.g. the training database may have a disproportionately large representation of heavy footed individuals, etc.). Large amounts of training data can be synthesized for any selected activity, based on empirical data of the selected activity to base the synthesized data on. Using the synthesized data may reduce the amount of empirical data necessary to train a NN for use on a given subject. Using the synthesized data may mitigate over-fitting of the NN.

Training the NN may include initial population training based on training data to initialize the weights and biases. In such cases, training the NN may also adjust the weights and biases based on subject training, and adjusting the weights and biases based on the subject training may precede applying the NN to pressure data outside the context of the subject training. The training data may be updated with reference to the outcome of the subject training.

Processing of the classified activity data through the NN, the population training or the subject training may be applied after inputting user data with an input module. The user data may define specific attributes of the subject and otherwise relate to the subject. Where the subject is an individual, user data may include personal attributes of the subject that may affect the activity classification output by the NN (e.g. weight, height, age, diabetes, physical injuries, arthritis, Parkinson's, any other physical or mental conditions etc.). The user data may be applied to selecting initial weights and biases based on the training data or other previous data. Population training or subject training may facilitate application of the NN for classifying activity performed by the subject over a session of a few seconds by taking into account personal attributes specific of the subject. If the subject changes activities during the session, the NN may classify multiple activities types performed during the session. The NN may also classify transitions from one activity type to the next, and between separate occurrences of one activity type.

The method and system described herein may use pressure data alone or may use pressure data and other input data.

The method and system described herein may be applied to classify fall predictors, the risk of falling, limb strain related to falling, or combinations thereof.

The method and system described herein may be used to determine optimal shoe fitting, automatic shoe fitting, automatic shoe lacing, adjusting orthotics, cast fitting, adjusting fit of devices applying pressure to the body.

The method and system described herein may be used to classify differences in the same activity such as balance metrics, or centre of pressure etc. Differences in the same activity may highlight differences associated with concussion.

The method and system described herein may be used to classify the risk for foot ulceration.

The method and system described herein may be used to support diagnosis of illness or disease (such as spinal chord lesions or injury, osteoarthrosis, Parkinson's etc.) based on quality of movement.

The method and system described herein may be used in user rehabilitation such as from a stroke, a traumatic brain injury or from neurological deficits.

The method and system described herein may be used as a tool to support diagnosis of neuropathy or quantification of disease based on gait changes.

The method and system described herein may be used as to support diagnosis of gait abnormalities and deviations attributed to neurological conditions such as hemiplegic, spastic diplegic, neuropathic, myopathic, Parkinsonian, choreiform, ataxic (cerebellar), and sensory gait.

The method and system described herein may be used support diagnosis of gait abnormalities such as antalgic gait, Charlie Chaplin gait, circumduction gait, limping, Lateral sway, Step variability, Internal rotation, or external rotation.

The method and system described herein may be used support diagnosis of a previous amputation such as transtibial, transfemoral, knee disarticulation, hip disarticulation, transmetatarsal, ray amputation, Chopart, Lisfranc, or ankle disarticulation The method and system described herein may be used to classify or predict energy expenditure based on gait and movement.

The method and system described herein may be used to classify or predict blood glucose, insulin requirements or combinations thereof based on gait and movement of the user. Classification of how orthotics affect gait, how orthotics strain the sensors, to monitor orthotics for initial fit or for ongoing assessment of fit may be facilitated by the method and system described herein. The method and system described herein may also be used for other equipment such as braces, retainers, prosthetics, prosthetic joints, slings, casts, or other medical appliances that may apply a pressure to the user or appliances that the user may apply pressure to, monitoring initial fit, monitoring ongoing compliance of fit, monitoring degradation, monitoring activity post implantation or combinations thereof.

The method and system described herein may be used for ergonomics such as adjusting seat fit in a vehicle, workstation fit, equipment fitting, military gear fitting, helmet fitting, bra fitting.

The method and system described herein may be used to classify impairment such as for use in police service testing, occupational health and safety, fatigue monitoring, long haul trucking testing and pilot testing.

The method and system described herein may be used for adjusting seat fit such as adjusting the seat in a vehicle, fitting the seat for various users, identifying the person in the seat, adjusting the fit before, during, or after driving, automatically adjusting the fit to the body pressures of a user or combinations thereof. The classification can be used for fit to car seats, bike seats, office chairs, wheelchairs, hospital beds, or any chairs or beds that a user applies pressure to when sitting in or lying on.

The method and system described herein may be used for classification for user identification based on fingerprint, palm print, handprint, foot print, face print, walking across a mat, pressure signature on any body part, pressure signature from any body part or combinations thereof. The identification can be individual signature identification or identification of subsets such as gender, weight category, or other demographic attributes.

The method and system described herein may be used for training and coaching of physical activities to give the user feedback. Feedback may be given on form, weight distribution, centre of gravity, hand placement, etc. Feedback may be given in real time or post-activity. Applications may include golf swing improvement with sensors in shoes, gloves or handle, with video or combinations thereof. Feedback may be reviewed by an expert, may include a web portal for an expert to classify data to create a training data set or combinations thereof.

The method and system described herein may be used for classifying efficiency of physical activities, determining efficiency rating, measuring rhythm, pace, and explosiveness, to predict a subject's performance on the activity.

The method and system described herein may be used for learning activities based on the subject's pressures, physical activity inputs and combinations thereof.

The method and system described herein may be used for automatic adjustment of vehicle parts such as tire valve cap, tire pressure, wheel rotations, etc. based on pressure sensor data.

The method and system described herein may be used in robotic surgery for determination of anatomical structure based on mechanical properties as determined by pressure sensors on instrument tips or other sensors or combinations thereof.

FIG. 1 shows a schematic of an activity classification system 10 for classifying input data 20 including pressure data resulting from activities performed by a subject. A sensor module 11 and an input module 16 receive the input data 20 and communicate the input data 20 to a processor 18. The processor 18 applies a deep learning neural network that is a convolutional neural network 30 ("CNN") to the input data 20 for classifying the subject's activity and resulting in classified activity data 38 that may be expressed in any suitable form. A variety of approaches may be used in presenting the classified activity data. Softmax is a function that normalizes probabilities to a range between 0 and 1, and may be used in the final layer of a NN for final classification and allows multi-possibility classification rather than binary. For example, with Softmax, probabilities of 0.8 running, 0.2 walking could be obtained rather than just 1.0 running, 0.0 walking. Other than Softmax, a sigmoid function, which would be binary only, or any other suitable normalization functions may be applied to present the classified activity data 38.

The input data 20 may also be applied to training the CNN 30. The processor 18 communicates the classified activity data 38 to an activity data module 40. The activity data module 40 may include a communication module 42 for communicating the classified activity data 38 to a user or a storage module 44 for storing the classified activity data 38. The input data 20 may be provided to the processor 30 through a temporary storage module prior to any processing (e.g. a transitory local computer readable medium, a transitory cloud-based storage, etc.).

The sensor module 11 includes a first pressure sensor 12 and a second pressure sensor 14 for receiving sensor data. The first pressure sensor 12 and the second pressure sensor 14 are positioned on a support matrix 15. The first pressure sensor 12 receives first pressure data 22. The second pressure sensor 14 receives second pressure data 24. A system may include more than two pressure sensors (e.g. the system 110, etc.) or only the first pressure sensor (e.g. the system 210, etc.). The first pressure sensor 12, the second pressure sensor 14, and the input module 16 may provide input data 20 to the processor 18. The first pressure sensor 12 and the second pressure sensor 14 may be combined with other sensors, as may be suitable for the application in respect of which the system 10 is applied (e.g. an accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, drug level sensor, or any other type of sensor that measures the level of impairment, etc.). The first pressure sensor 12 or the second pressure sensor 14 may be either binary pressure sensors with a defined threshold for a positive reading, or may be sensors that detect a pressure or force value.

The first pressure sensor 12 and the second pressure sensor 14 may be located on the support matrix 15 at corresponding locations for measuring pressure at a location on the subject's body and resulting from activities selected consistent with a particular application (e.g. at portions of an insole corresponding to a ball of a foot, portions of an insole corresponding to a heel of a foot, portions of an insole corresponding to a ball of a foot and a heel of a foot, fingertips of a glove, fingers of a glove, palm of a glove, elbow pads, knee pads, etc.). The first pressure data 22 and the second pressure data 24 include data of measured pressure at the locations of the first pressure sensor 12 and the second pressure sensor 14 when worn by the subject.

The input module 16 is for providing user commands and user data 26 to the processor 18. The user data 26 may include specific attributes of the subject. Where the subject is an individual, the specific attributes may include personal attributes such physical traits, mental traits, or other data related to the subject that are to applied by the CNN 30 in determining the classified activity data 38. For example, factors such as weight, height, age, any physical or mental conditions (e.g. diabetes, physical injuries, arthritis, Parkinson's, etc.), or other factors that may affect the activity classification output by the CNN 30, may be included in the user data 26. The user data 26 may be applied as part of the input data 20, or may be used downstream of classified activity data 38 to define features calculated with reference to both the classified activity data 38 and the user data 26 separately (e.g. as in the systems 410 and 510, etc.).

Figure 2:
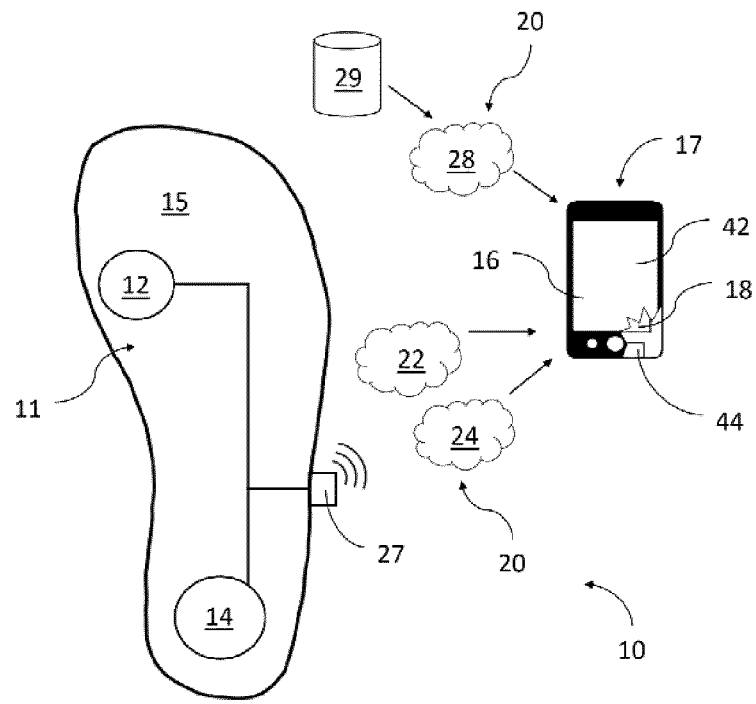
FIG. 2 is a schematic of the system of FIG. 1 configured for receiving pressure data along the sole of a user.

FIG. 2 shows a schematic of the activity classification system 10 adapted for use on a sole of a subject individual's foot. For such applications, the support matrix 15 may be in the shape of an insole, the first pressure sensor 12 may be located on the support matrix 15 at a location corresponding to the ball of the foot, and the second pressure sensor 14 may be located on the support matrix 15 at a location corresponding to the heel of the foot. Functions provided by the input module 16, the processor 18, and the activity data module 40, may be executed on or accessed through a first device 17 with reference to locally stored or remotely accessed data and processes. The first device 17 in the system 10 as shown in FIG. 2 is exemplified by a smartphone, but any suitable mobile or other device may be applied (e.g. smartphone, smartwatch, tablet, laptop computer, desktop computer, cloud-based server etc.). The sensor module 11 may include an inertial sensor connected with a dorsal surface of the subject's shoe (not shown; an example of a system with a sensor other than a pressure sensor is the system 410, which includes to the other sensor 409, which in the system 410 is an inertial sensor). The first pressure data 22 and the second pressure data 24 are transmitted from the sensor module 11 to the first device 17 by a wireless transmitter 27.

The processor 18 is configured for executing instructions for applying the CNN 30 to the input data 20. The CNN 30 provides an activity classification process, resulting in the classified activity data 38. The processor 18 may be located on any suitable mobile or other device (e.g. smartphone, smartwatch, tablet, laptop computer, desktop computer, cloud-based server etc.). Communication between the processor 18 and the first pressure sensor 12, the second pressure sensor 14, and the input module 16, may be through any wired or wireless connection. In FIG. 2, the first pressure data 22 and the second pressure data 24 are shown being communicated to the first device 17 through a wireless connection. The processor 18 may be a graphics processing unit, a standard central processing unit, or any suitable processing unit.

Returning to FIG. 1, the CNN 30 includes at least one convolutional layer 32 and at least one fully connected layer 34. The input data 20 is received by the processor 18. The input data 20 may include training data 28. The training data 28 may be accessed from a training database 29 accessed through a wired connection, through a wireless connection, from a remote service, or by any suitable access method. The training data 28 is received by the processor 18 with the input data 20 and may be provided to the CNN 30 to train the CNN 30. The training data 28 may include empirical pressure data from a plurality of other subjects, including subjects having similar or different specific attributes compared with the current subject as determined with reference to the user data 26, the first pressure data 22, the second pressure data 24, or any data received by the sensor module 11.

The convolutional layer 32 may be applied to the first sensor data 22, the second sensor data 24 and the user data 26 with reference to weights and biases 36. The training data 28 may include empirical pressure data of the other subjects each performing a plurality of activities. The convolutional layer 32 may be applied to the training data 28 and the user data 26 with reference to the weights and biases 36. The weights and biases 36 may be determined and updated with reference to the input data 20, including the first sensor data 22, the second sensor data 24, the user data 26, the training data 28 or the classified activity data 38. The input data 20 is convoluted and pooled in the convolutional layer 32, then provided to the fully connected layer 34, resulting in the classified activity data 38.

A confirmation input 47 may be received from the input module 16 by the processor 18 and applied to train the CNN 30 based on classified activity data 38 resulting from the first pressure data 22 and the second pressure data 24 acquired from the first pressure sensor 22 and the second pressure sensor 24. Similarly, a training confirmation 45 may be received from the training database 29 by the processor 18 and applied to train the CNN 30 based on classified activity data 38 resulting from the training data 28 received from the training database 29. Either of the confirmation input 47 or the training confirmation 45 may provide actual classified activity data for comparing with the classified activity data 38 and training the CNN 30. The classified activity data 38 may be applied to train the CNN 30 by updating the weights and biases 36 as part of training the CNN 30. The classified activity data 38 may be communicated to the activity data module 40 for feedback to be provided to the user through the communication module 42 based on the classified activity data 38. The activity data module 40 may allow for further processing and review of the classified activity data 38 through the storage module 44. The classified activity data 38 may be provided to a database for accessing in subsequent rounds of training and as part of the training data 28. In some cases, the training may be carried out with reference to the training data 28 as part of configuration or updating of the system 10, and some such systems may function without application of the subject training.

Figure 3:
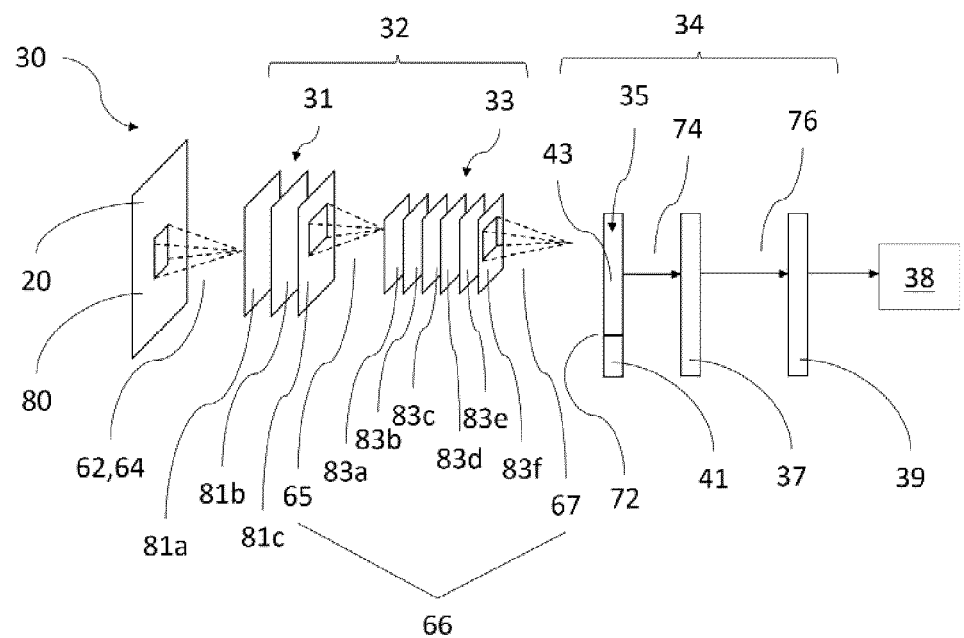
FIG. 3 is a schematic of a CNN used in the system of FIG. 1.

FIG. 3 is a schematic of the CNN 30 processing the input data 20 into the classified activity data 38. The input data 20 is passed through two convolutional layers 32 and three fully-connected layers 34 during activity classification to provide the classified activity data 38. The two convolutional layers 32 include a first convolutional layer 31 and a second convolutional layer 33. The three fully-connected layers 34 include a first fully-connected layer 35, a second fully-connected layer 37, and a third fully-connected layer 39. Each of the convolutional layers 32 and the fully-connected layers 34 includes nodes located on each feature map of the convolutional layer 32 or the fully-connected layer 34.

Nodes each include a datum or a greater portion of the input data 20. A node may be connected to one or more nodes in an immediately subsequent or precedent layer. Connections between nodes are defined by an activation function and subject to the weights and biases 36 applicable to the convolutional step of a particular connection, including as described above with reference to Eq. 1. The weights and biases 36 determine the connections between the nodes in subsequent and precedent convolutional layers 20 based on the input data 20 and the relationships between the nodes. The user data 26 may be provided to the processor 18 for application in the CNN 30 to determine initial weights and biases 36, and in turn the relationships between nodes in adjacent layers. The weights and biases 36 may apply to relationships between nodes in adjacent convolutional layers 32, such as between the first convolutional layer 31 and the second convolutional layer 33. The weights and biases 36 may apply to relationships between nodes in a convolutional layer 32 and nodes in an adjacent fully connected layer 34, such as between the second convolutional layer 33 and the first fully connected layer 35. The weights and biases 36 may apply to relationships between nodes in an adjacent fully connected layers 34, such as between the first fully connected layer 35 and the second fully connected layer 37.

The input data 20 is presented as a data matrix 80, shown as a two dimensional data array. Each of the convolutional layers 32 may apply one or more filter masks to the data matrix 80. Each separate filter mask may apply separate weights and biases, and resulting in a feature map for each filter mask and each set of weights and biases. The first convolutional layer 31 may include a first feature map 81$a$, a second feature map 81$b$, and a third feature map 81$c$, which result from applying three separate filter masks to the data matrix 80. The second convolutional layer 33 may include a first feature map 83$a$, a second feature map 83$b$, a third feature map 83$c$, a fourth feature map 83$d$, a fifth feature map 83$e$ and a sixth feature map 83$f$, which result from applying filter masks to each of the first feature map 81$a$, a second feature map 81$b$, and a third feature map 81$c$. Nodes of the input data 20 may be defined on the data matrix 80.

The data matrix 80 may be represented as a matrix including a plurality of 1-dimensional vectors of the input data 20 for the first pressure sensor 22 and the second pressure sensor 24, with each vector representing the recorded values over time from one of the sensors. In the CNN 30, the features maps 81$a$, 81$b$ and 81$c$ of the first convolutional layer 31, and the feature maps 83$a$, 83$b$, 83$c$, 83$d$, 83$e$ and 83$f$ of the second convolutional layer 33 are abstracted from the representation of sensor data as a one-dimensional vector in time, in the data matrix 80.

The data in the fully connected layers 34 may be defined as a 1-dimensional vector in which each value is linked to every value in a subsequent fully connected layer through an activation function that includes the weights and biases 36.

The CNN 30 may be applied to the input data 20 during a convolutional step 62. During the convolutional step 62, the values in the input data 20 that meet the qualifications of an activation function for a convolutional step are multiplied by a weight and summed with a bias. Following the convolutional step, a pooling step 64 is applied to recover a datum and some of its neighbours in the data matrix 80 for promotion to the feature maps 81*a*, 81*b* and 81*c* of the first convolutional layer 31. During the convolutional step 62, the data is multiplied by a weight, amplifying the amount of data. Pooling data during the pooling step 64 lowers the resolution and amount of the data in the convolutional layer, preserving bandwidth with respect to the data in the data matrix 80 following the convolutional step 62. The convolutional step 62 and the pooling step 64 may draw correlations over time only and from one individual sensor per data matrix 80 of the input data 20, or may draw correlations across multiple sensors per data matrix 80 of the input data 20.

The pooling step 64 may include max pooling, wherein the maximum value of a node and its neighbours is promoted as a single or reduced data sampling of all values at and close to the node that were promoted through the activation function at the convolutional step 62. The pooling step 64 may include minimum pooling, wherein the minimum value of a node and its neighbours is promoted as a single or reduced data sampling of all values at and close to the node that were promoted through the activation function at the convolutional step 62. The pooling step 64 may include mean pooling, wherein the mean value of a node and its neighbours is calculated and a resulting mean value promoted as a single or reduced data sampling of all values at and close to the node that were promoted through the activation function at the convolutional step 62.

Application of the convolutional step 62 and the pooling step 64 to the input data 20 results in the first feature map 81*a*, the second feature map 81*b*, and the third feature map 81*c* of the first convolutional layer 31. Subsequent convolutional and pooling steps 66 may be applied to the feature maps of the convolutional layers 32. The subsequent convolutional and pooling steps 66 may include first subsequent convolutional and pooling steps 65 and second subsequent convolutional and pooling steps 67.

Application of the first subsequent convolutional and pooling steps 65 to the nodes in the first feature map 81*a*, the second feature map 81*b*, and the third feature map 81*c* of the first convolutional layer 31 results in the first feature map 83*a*, the second feature map 83*b*, the third feature map 83*c*, the fourth feature map 83*d*, and the fifth feature map 83*e* of the second convolutional layer 33.

After the features maps of the convolutional layers 32 have been defined, the input data 20 may be filtered through the fully-connected layers 34. Application of the second convolutional and pooling step 67 to the nodes in the first feature map 83*a*, the second feature map 83*b*, the third feature map 83*c*, the fourth feature map 83*d*, and the fifth feature map 83*e* results in a convolutional portion 43 of the first fully-connected layer 35. The user data 26 may be concatenated with the convolutional portion 43 of the first fully-connected layer 35 during a concatenation step 72, defining a subject attribute portion 41 of the first fully-connected layer 35.

All nodes of data on the first fully connected layer 35 may be expressed as a first one-dimensional vector, which may be processed through an activation function of a first connection step 74, resulting in the second fully-connected layer 37. Similarly, all nodes of data on the second fully connected layer 37 may be expressed as a second one-dimensional vector, which may be processed through an activation function of a second connection step 76, resulting in the third fully-connected layer 39. A vector of the third fully-connected layer 39 may be expressed at the classified event data 38. The activation functions of the first connection step 74 and the second connection step 76 are calculated based on the results of the feature maps prepared from multiple convolution and pooling steps during the convolutional layers, and do not include pooling steps.

Figure 4:
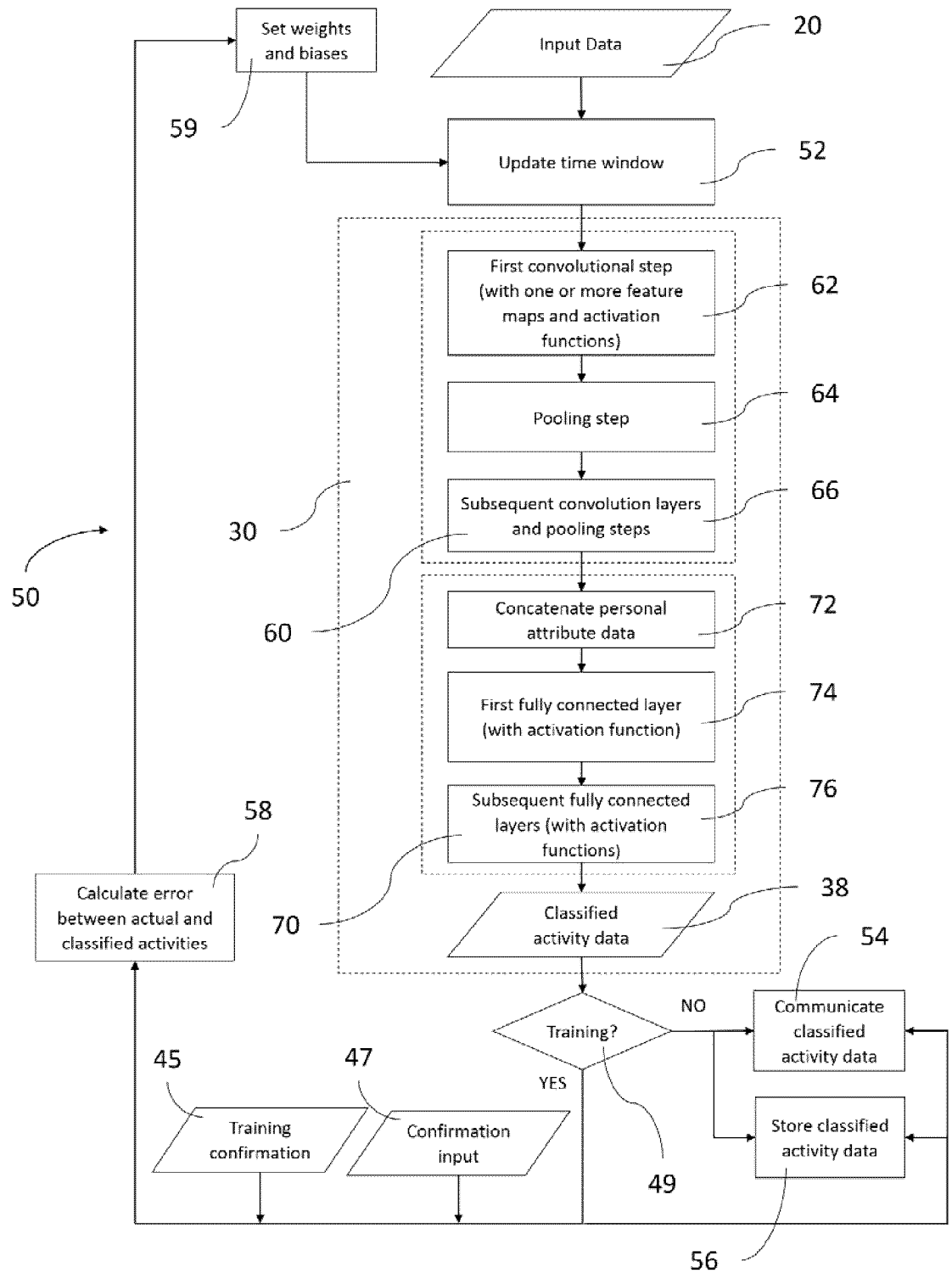
FIG. 4 is a flowchart of a method for classifying physical activities of a user with the CNN of FIG. 3 and training the CNN.

FIG. 4 is a schematic of a method of activity classification 50 using the CNN 30 and the system 10. A time window (see the time window 73 of FIG. 5) of known duration is defined on a timeline of the input data 20. The input data 20 within the time window is processed to provide the classified activity data 38. Updating the time window 52 may include initially defining the time window on the input data 20 or progressing the time window along the timeline of the classified activity data 38. Distinct portions of the classified activity data 38 timeline within the time window may be overlapping in time. Convolutional filtering 60 and fully-connected filtering 70 are applied to the input data 20 within the time window, resulting in the classified activity data 38. A training query 49 determines whether to check the classified activity data 38 against the confirmation input 47. Regardless of the outcome at the training query 49, the method 50 includes is communicating the classified activity data to a user 54 or storing the classified activity data 56. The confirmation input 47 may be applied to training based on input data 20 that includes the first pressure data 22 or the second pressure 24. The training confirmation 45 may be applied to training based on input data that includes training data 28. Based on the classified activity data 38 and the confirmation input 47 or the training confirmation 45, a loss function is calculated between the classified and actual activities 58, which may be applied to setting weights and biases 59. After setting the weights and biases 59, additional input data 20 may be received and applied to the convolutional filtering 60 and the fully-connected filtering 70.

The input data 20 may include the first pressure data 22, the second pressure data 24, the user data 26, or the training data 28, which may be represented as the data matrix 80. After updating the time window 52, the input data 20 is applied to the first convolutional step 62 and the first pooling step 64 of the first convolutional layer 31. The subsequent convolutional steps and pooling steps 66 of the second convolutional layer 33 and any subsequent convolutional layers are also applied.

User input data 26 may be concatenated onto a fully-connected layer at the concatenation step 72. Data in a feature map following the convolutional filtering 60 may be applied to the first fully-connected layer 35, which includes the user input data 26, and to any subsequent fully-connected steps 76 of the fully-connected filtering 70. The fully-connected filtering 70 results in the classified activity data 38, which may be communicated to a user 54 or stored 56. The error between the actual and classified activities may be calculated though subject training with reference to the classified activity data 38 based on the first pressure data 22, the second pressure data 24 and any additional empirical data obtained during the moving-window subset of time. The error between the actual and classified activities may be calculated though population training with reference to the classified activity data 38 based on the training data 28. The training may be applied to setting the weights and biases 59.

Figure 5:
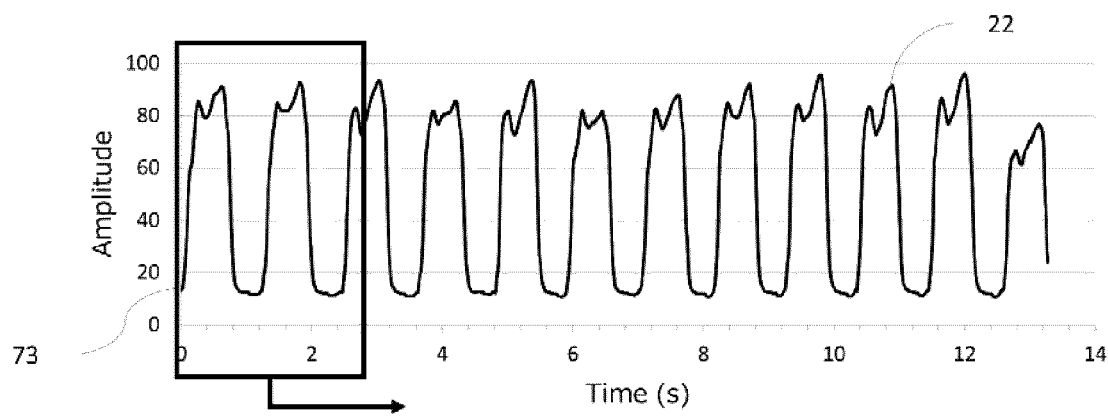
FIG. 5 is a plot of example pressure data acquired with the system of FIG. 1 being processed with a time window.

FIG. 5 shows input data 20 that is pressure data and a time window located over the pressure data to defined a portion of the pressure data to which the NN will be applied.

Figure 6:
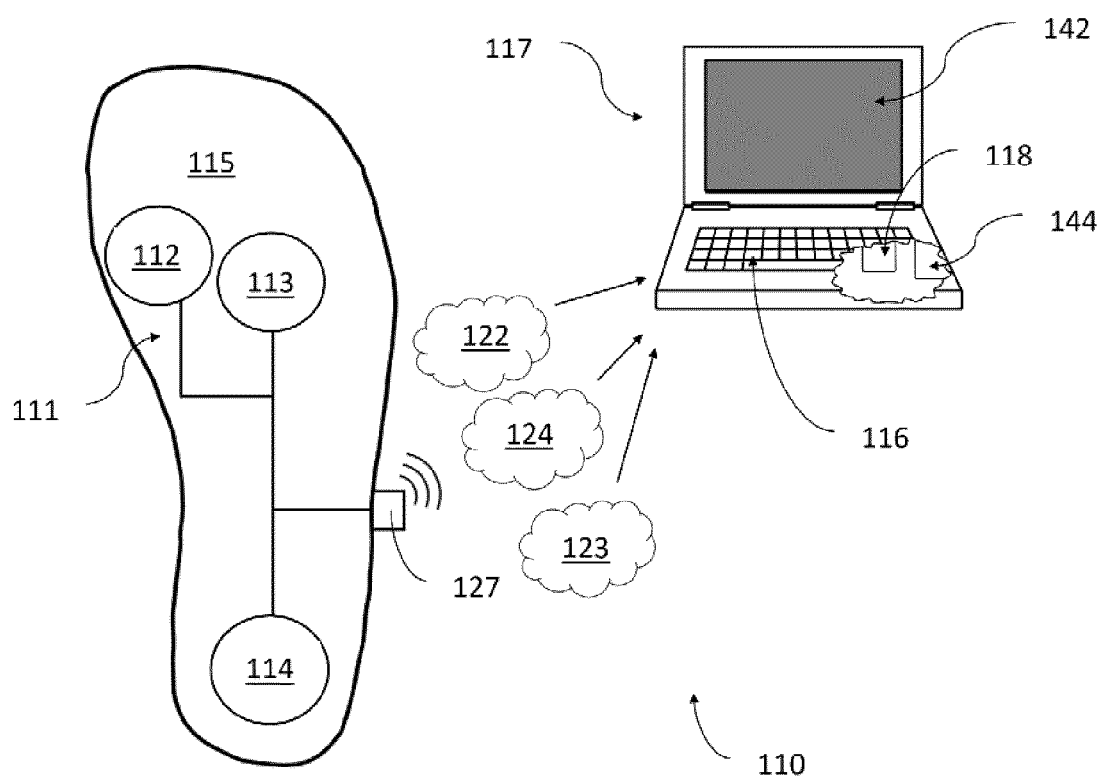
FIG. 6 is a schematic of a system for receiving pressure data along the sole of a subject.

FIG. 6 is a schematic of a system 110 for activity classification.

Figure 7:
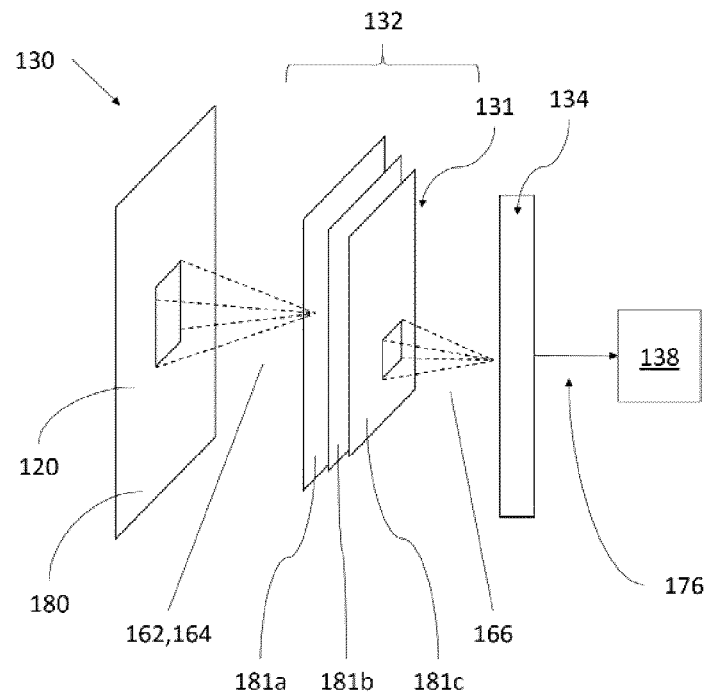
FIG. 7 is a schematic of a CNN used in the system of FIG. 6.

FIG. 7 is a schematic of a CNN 130 processing the input data 120 into the classified activity data 138.

The system 110 includes the first pressure sensor 112, the second pressure sensor 114, and a third pressure sensor 113. The wireless transmitter 127 transmits the first pressure data 122, the second pressure data 124, and third pressure data 123 to the first device 117, shown as a laptop computer, for processing by the processor 118 by application of the CNN 130. The first device includes the communication module 142 and the storage module 144. The training data (not shown) and training database (not shown) may be stored directly on the storage module 144 for local access without remote access, as with the training database 29 of the system 10. The system 110 may also be used without any training database, wherein the supervised training is entirely user training.

The CNN 130 includes a single convolutional layer 132 and a single fully-connected layer 134. The convolutional step 162 with three different filter masks, and the pooling step 164 are applied to the data matrix 180 of the input data 120, resulting in the first feature map 181$a$, the second feature map 181$b$, and the third feature map 181$c$ of the convolutional layer 132. The subsequent convolutional and pooling steps 166 are applied to the first feature map 181$a$, the second feature map 181$b$, and the third feature map 181$c$ of the convolutional layer 132, providing the first fully-connected layer 134. The first connection step 176 is applied to the fully-connected layer 134, resulting in the classified activity data 138.

The increased number of pressure sensors on the system 110 compared with the system 10 may facilitate data classification with fewer convolutional and pooling steps, and fewer fully-connected steps, in the system 110 compared with the system 10.

Figure 8:
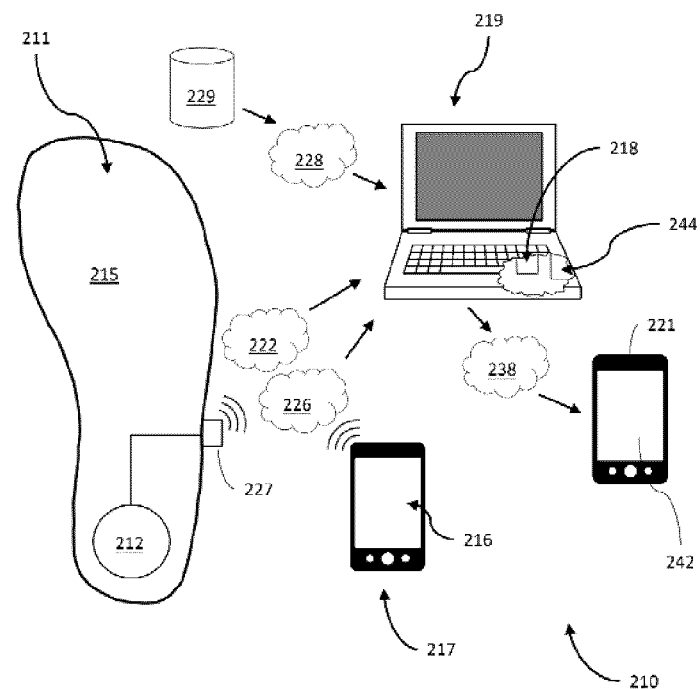
FIG. 8 is a schematic of a system for receiving pressure data along the sole of a subject.

FIG. 8 is a schematic of a system 210 for activity classification. The sensory module 211 includes only the first sensor 212. The first device 217 includes the functions of the input module 216, and is shown as a first smartphone. The first pressure data 222 is transmitted from the sensor module 211 to a second device 219, shown as a laptop computer. The second device includes the processor 218 and the storage module 244. The user data 226 is transmitted to the second device 219 by the first device 217. The second device 219 accesses the training database 229 for providing the training data 228 to the second device 219. The classified activity data 238 may be stored on the storage module 244 and also transmitted to a third device 221, shown as a smartphone, which may provide the function of the communication module 242.

Figure 9:
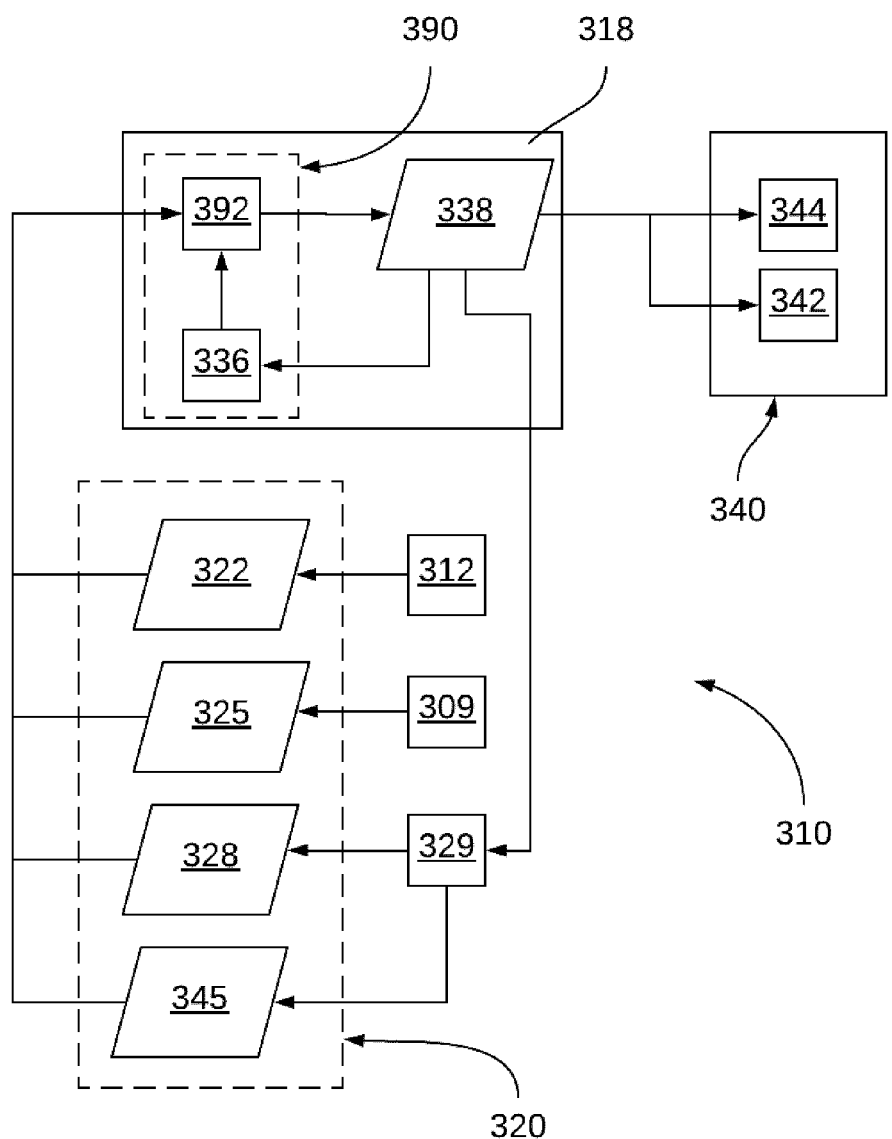
FIG. 9 is a block diagram illustrating selected hardware and process components of an activity classification system using a NN.

FIG. 9 shows a schematic of an activity classification system 310 for classifying the input data 320 including the pressure data 322 resulting from activities performed by the subject. The first pressure sensor 312, an other sensor 309 and the training database 329 generate the input data 320. The input data 320 is communicated to the processor 318. The processor 318 applies a deep learning neural network ("NN") 390 to the input data 320 for classifying the subject's activity and resulting in classified activity data 338 that may be expressed in any suitable form. The input data 320 may also be applied to training the NN 390. The processor 318 communicates the classified activity data 338 to the activity data module 340. The activity data module 340 may include the communication module 342 for communicating the classified activity data 338 to a user or the storage module 344 for storing the classified activity data 338. The input data 320 may be provided to the processor 318 through a temporary storage module prior to any processing (e.g. a transitory local computer readable medium, a transitory cloud-based storage, etc.).

The sensors include the pressure sensor 312 and the other sensor 309 for receiving the input data 320. The other sensor 309 may include any suitable sensor that measures data indicative of physical activity or other relevant factors (e.g. an accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, drug level sensor, or any other type of sensor that measures the level of impairment, etc.). The pressure sensor 312 generates pressure data 322. The other sensor 309 receives other sensor data 325. The pressure sensor 312 and the other sensor 309 may be combined with other sensors, as may be suitable for the application in respect of which the system 310 is applied. The pressure sensor 312 or the other sensor 309 may be either binary sensors with a defined threshold for a positive reading, or may be sensors that detect a quantitative value.

The input data 320 is received by the processor 318. The input data 320 may include the training data 328. The training data 328 may be accessed from the training database 329 accessed through a wired connection, through a wireless connection, from a remote service, or by any suitable access method. The training data 328 is received by the processor 318 with the input data 320 and may be provided to the NN 390 to train the NN 390. The training data 328 may include empirical pressure or other data from a plurality of other subjects, including subjects having similar or different specific attributes compared with the current subject. The training data 328 may include synthetic data generated from empirical pressure or other data from a plurality of other subjects, including subjects having similar or different specific attributes compared with the current subject. The training data 328 may include simulated pressure data or other data.

The training confirmation 345 may be received from the training database 329 by the processor 318 and applied to train the NN 390 based on the classified activity data 338 resulting from the training data 328 received from the training database 329. The training confirmation 345 may provide actual classified activity data for comparing with the classified activity data 338 and training the NN 390.

The classified activity data 338 may be communicated to the activity data module 340 for feedback to be provided to the user through the communication module 342 based on the classified activity data 338. The activity data module 340 may allow for further processing and review of the classified activity data 338 through the storage module 344. The classified activity data 338 may be provided to the training database 329 for accessing in subsequent rounds of training and as part of the training data 328. In some cases, the training may be carried out with reference to the training data 328 as part of configuration or updating of the system 310, and some such systems may function without application of the subject training.

Figure 10:
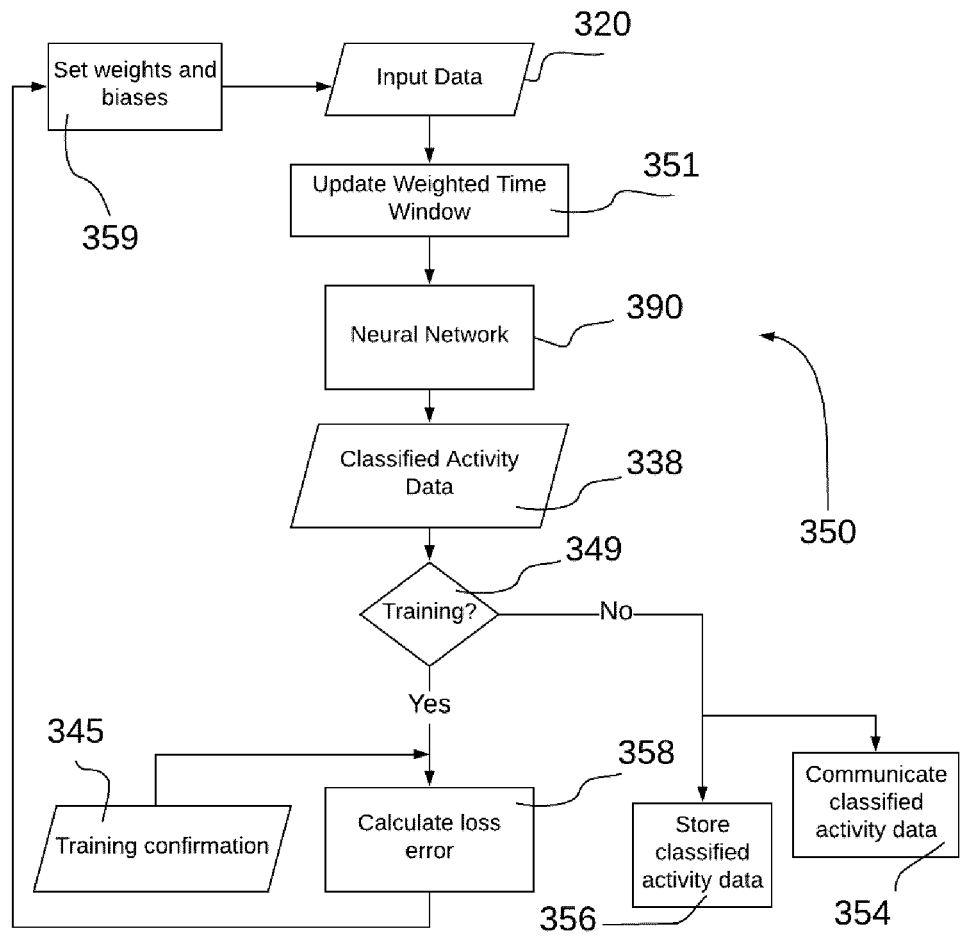
FIG. 10 is a flowchart of a method for classifying physical activities of a user with the NN of FIG. 9 and training the NN.

FIG. 10 is a flowchart of a method 350 for activity classification using the system 310. A weighted time window (weighted time window 357 shown in FIG. 11) is defined for the input data 320. The weighted time window 357 is of a defined duration in time, and certain aspects of the input data 320 within the weighted time window 357 are assigned greater significance when being processed by the NN 390. The portions of the input data 320 within the weighted time window 357 as it is progressed across a timeline of the input data 320 may overlap. The method 310 includes updating the weighted time window 351. Updating the weighted time window 351 may include defining the weighted time window 357 for the input data 320, changing the weighting features of the weighted time window or progressing the weighted time window 357 along the timeline of the input data 320.

The NN 390 is applied to the input data 320, resulting in the classified activity data 338. The training query 349 provides a decision point to determine whether to check the classified activity data 338 against the training confirmation 345. Where no training is to take place based on the classified activity data 338, the system 310 communicates the classified activity data 338 to a user 354 or stores the classified activity data 356.

Where the system 310 is applying the training data 328 as the input data 320 and is training based on the resulting classified activity data 338 and the training confirmation 345, the loss function is calculated 358. The loss function is based on the difference between the classified activity data 338 of the training data 328 and the training confirmation 345. The loss function may be applied to setting weights and biases 359. After setting the weights and biases 359, additional input data 320 may be received and applied to the neural network 390.

Figure 11:
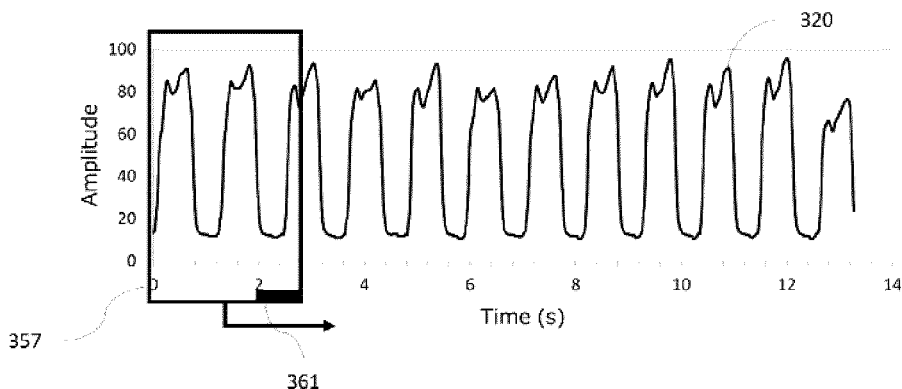
FIG. 11 is a plot of example pressure data acquired with the system of FIG. 9 being processed with a weighted time window.

FIG. 11 shows the input data 320 and the weighted time window 357 superimposed over the input data 320 to defined a portion of the input data 320 to which the NN 390 will be applied to provide the classified activity data 338. A weighted portion 361 of the input data 320 within the weighted time window 357 may be weighted more heavily than the remainder of the input data 320 within the weighted time window 357 when applying the NN 390 to the input data 320 after the input data 320 is filtered through the weighted time window 357.

Figure 12:
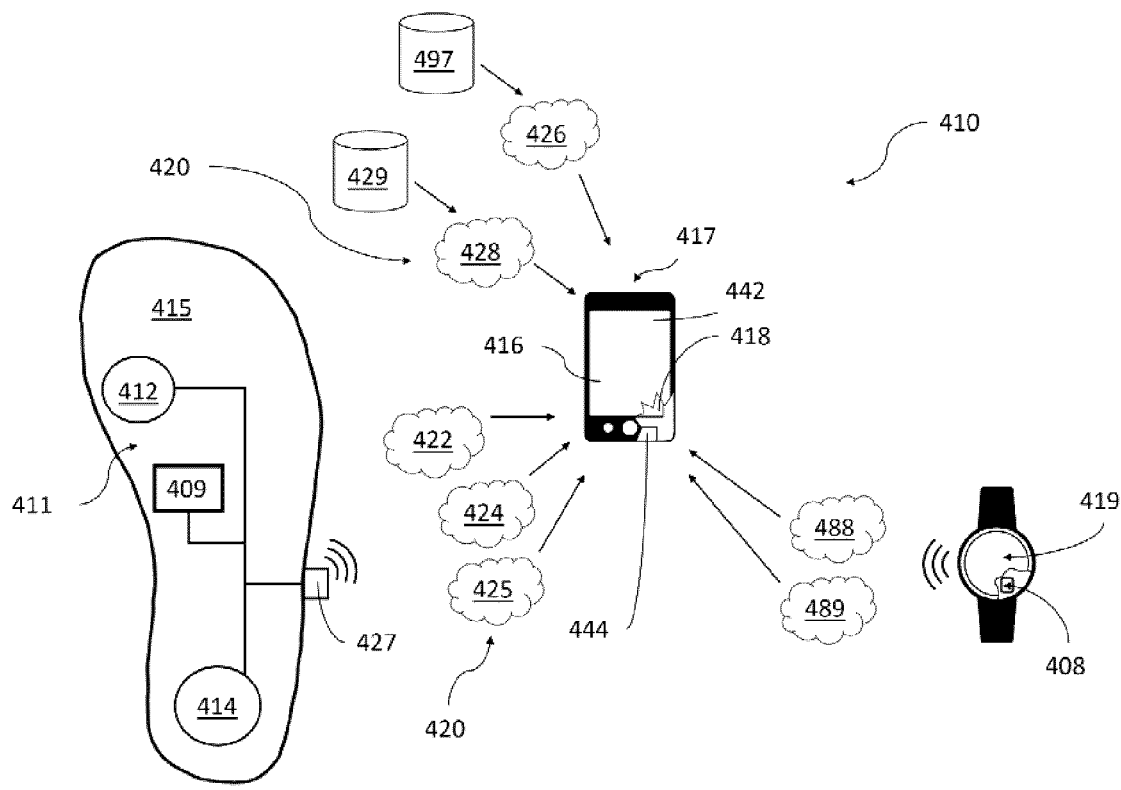
FIG. 12 is a schematic of a system for receiving pressure data along the sole of a subject and receiving blood glucose data from the subject.

FIG. 12 is a schematic of an activity classification system 410 for classifying the input data 420 resulting from activities performed by the subject. The sensor module 411 and the training database 429 provide the input data 420. The input data 420 is processed by the processor 418 on the first device 417, which is shown as a smart phone. The sensor module 411 is located on the support matrix 415. The communication module 442 communicates the classified activity data 438 (see FIG. 13) and classified combined metabolic and activity data, such as the energy expenditure data 487, to a user of the system 410, each of which may also be stored on the storage module 444. The user may be the subject wearing the insole with the support matrix 415 or a different individual. A health information database 497 is accessible from the first device 417 and a biological feature sensor 408 (e.g. a blood glucose monitor, a blood insulin monitor, a monitor for other metabolites in blood, a monitor for skin detectable metabolites, etc.) is present on the second device 419.

The sensor module 411 includes the first pressure sensor 412, the second pressure sensor 414 and the other sensor 409 on the support matrix 415 for receiving the input data 420. The other sensor 409 may include any suitable sensor that measures a level of physical activity or other variable accounted for by the NN 490 (see FIG. 13). The first pressure sensor 412 generates the first pressure data 422. The second pressure sensor 414 generates the second pressure data 424. The other sensor 409, in this case an inertial measurement unit ("IMU") receives the other sensor data 425, in this case shown as IMU data. The first pressure sensor 412, the second pressure sensor 414 and the other sensor 409 may be combined with additional sensors, as may be suitable for the application in respect of which the system 410 is applied. The first pressure sensor 412, the second pressure sensor 414 and the other sensor 409 may each be either binary sensors with a defined threshold for a positive reading, or may be sensors that detect a quantitative value.

The second device 419, shown as a smartwatch, includes the biological feature sensor 408. The biological feature sensor 408 receives insulin use data 488 or blood glucose data 489. The insulin use data 488 and the blood glucose data 489 are provided from the second device 419 to the first device 417 and the classified activity data 438 may be weighted alongside the insulin use data 488 or blood glucose data 489 to define the energy expenditure data 487. The health information database 497 may include formal medical records, user-inputted health information, or other relevant user data 426 that may also be weighted alongside the classified activity data 438. The input module 416 may be used to requisition updated user data 426 from the health information database 497 or to otherwise input information or commands for application in the system 410.

The input data 420 may include the training data 428. The training data 428 may be accessed from the training database 429 through a wired connection, through a wireless connection, from a remote service, or by any suitable access method. The training data 428 is received by the processor 418 with the input data 420 and may be provided to the NN 490 to train the NN 490. The training data 428 may include empirical pressure or other data from a plurality of other subjects, including subjects having similar or different specific attributes compared with the current subject. The training data 428 may include synthetic data generated from empirical pressure or other data from a plurality of other subjects, including subjects having similar or different specific attributes compared with the current subject. The training data 428 may include simulated pressure or other data. The training data 428 may be used to update the weights and biases applied in the NN 490.

Figure 13:
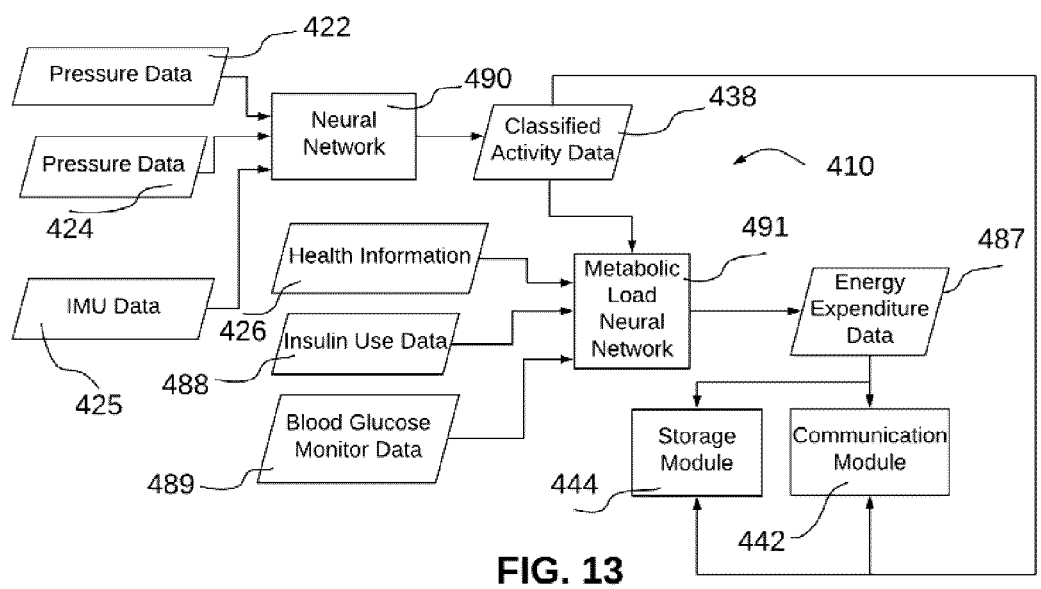
FIG. 13 is a block diagram of a system for classifying physical activities of a user with an activity classification NN and a metabolic load NN using the system of FIG. 12.

FIG. 13 is a schematic showing functionality of the activity classification system 410 directed to energy expenditure determination based on the classified activity data 438 in combination with the insulin use data 488, blood glucose data 489 and the user data 426 from the health database 497. The first pressure data 422, the second pressure data 424 and the IMU data 425 is input into activity classification network 490. The activity classification network 490 is applied to classify the input data 420 into classified activity data 438. A metabolic load neural network ("MLNN") 491 is applied to the classified activity 438 along with user data 426 including electronic medical records sourced from the health information database 497, insulin use data 488 or blood glucose monitor data 489, to determine the energy expenditure data 487. The energy expenditure data 487 is based both on the classified activity data 438, and on the insulin use data 488, blood glucose data 489 and the user data 426 from the health database 497. The classified activity data 438 may be communicated directly to a user at the communication module 442 or stored in the storage module 444, as classified activity data 438 alone or as part of the energy expenditure data 487, which may also be communicated directly to a user at the communication module 442 or stored in the storage module 444.

Figure 14:
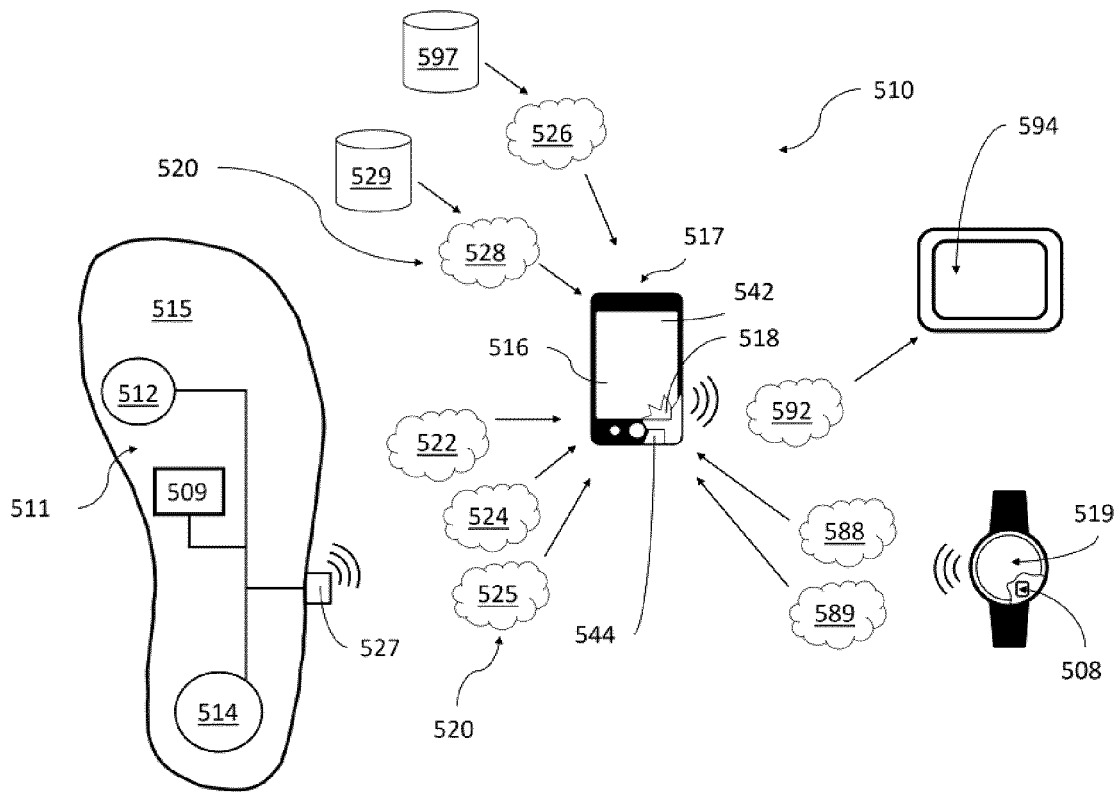
FIG. 14 is a system for receiving pressure data along the sole of a subject, receiving blood glucose data from the subject and administering insulin in response to the blood glucose data.

FIG. 14 is a schematic of an activity classification system 510 for classifying the input data 520 resulting from activities performed by the subject. The sensor module 511 and the training database 529 provide the input data 520. The input data 520 is processed by the processor 518 on the first device 517, which is shown as a smart phone. The sensor module 511 is located on the support matrix 515. The communication module 542 communicates the classified activity data 538 (see FIG. 15) and the energy expenditure data 587 to a user of the system 510, each of which may also be stored on the storage module 544. The user may be the subject wearing the insole with the support matrix 515 or a different individual. A health information database 597 is accessible from the first device 517 and a biological feature sensor 508 is present on the second device 519. A drug delivery system 594 is also in communication with the first device 517 for receiving insulin requirement data 592. Where the insulin requirement data 592 meets a defined metric, the drug delivery system 594 will administer insulin 594 to the subject. The biological feature sensor 508 and the drug delivery system 594 may be similarly adapted to measure other biological features and provide other medications or substances to the subject.

The sensor module 511 includes the first pressure sensor 512, the second pressure sensor 514 and the other sensor 509 on the support matrix 515 for receiving the input data 520. The other sensor 509 may include any suitable other sensor that measures a level of physical activity or other variable accounted for by the NN 590 (see FIG. 15). The first pressure sensor 512 generates the first pressure data 522. The second pressure sensor 514 generates the second pressure data 524. The other sensor 509, in this case an IMU, receives the other sensor data 525, in this case shown as IMU data. The first pressure sensor 512, the second pressure sensor 514 and the other sensor 509 may be combined with additional sensors, as may be suitable for the application in respect of which the system 510 is applied. The first pressure sensor 512, the second pressure sensor 514 and the other sensor 509 may each be either binary sensors with a defined threshold for a positive reading, or may be sensors that detect a quantitative value.

The second device 519, shown as a smartwatch, includes the biological feature sensor 508. The biological feature sensor 508 receives insulin use data 588 or blood glucose data 589. The insulin use data 588 and the blood glucose data 589 are provided from the second device 519 to the first device 517 and the classified activity data 538 may be weighted alongside the insulin use data 588 or blood glucose data 589 to define the energy expenditure data 587. The health information database 597 may include formal medical records, user-inputted health information, or other relevant user data 526 that may also be weighted alongside the classified activity data 538. The input module 516 may be used to requisition updated user data 526 from the health information database 597 or to otherwise input information or commands for application in the system 510.

The input data 520 may include the training data 528. The training data 528 may be accessed from the training database 529 through a wired connection, through a wireless connection, from a remote service, or by any suitable access method. The training data 528 is received by the processor 518 with the input data 520 and may be provided to the NN 590 to train the NN 590. The training data 528 may include empirical pressure or other data from a plurality of other subjects, including subjects having similar or different specific attributes compared with the current subject. The training data 528 may include synthetic data generated from empirical pressure or other data from a plurality of other subjects, including subjects having similar or different specific attributes compared with the current subject. The training data 528 may include simulated pressure or other data. The training data 528 may be used to update the weights and biases applied in the NN 590.

Figure 15:
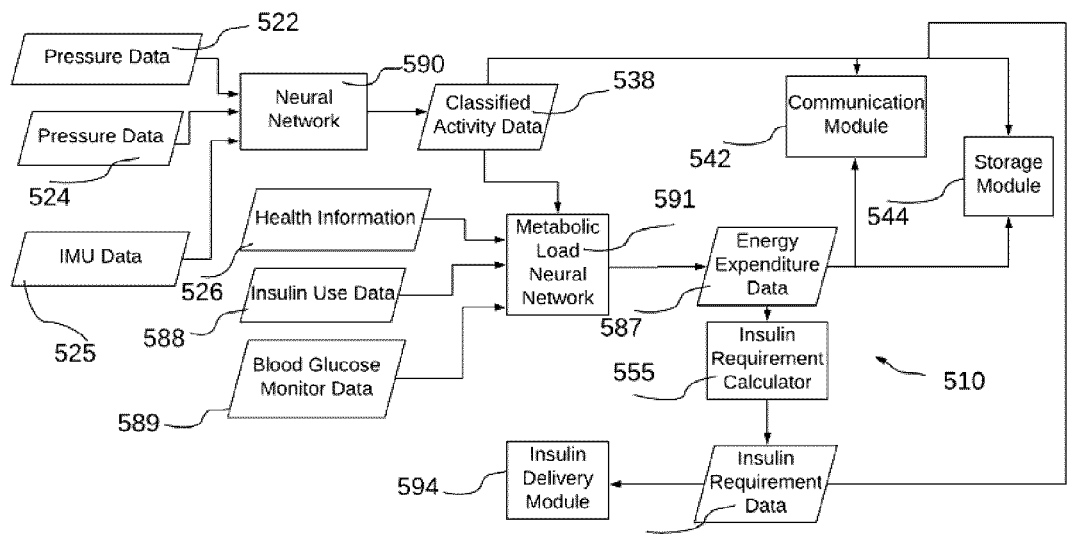
FIG. 15 is a block diagram of a system for classifying physical activities of a user with an activity classification NN cascaded a metabolic load NN, and administering insulin using the system of FIG. 14.

FIG. 15 is a schematic showing functionality of the activity classification system 510 directed to energy expenditure determination and administration of insulin, based on the classified activity data 538 in combination with the insulin use data 588, blood glucose data 589 and the user data 526 from the health database 597. The first pressure data 522, the second pressure data 524 and the IMU data 525 is input into activity classification network 590. The activity classification network 590 is applied to classify the input data 520 into classified activity data 538. The MLNN 591 is applied to the classified activity 538 along with user data 526 including electronic medical records sourced from the health information database 597, insulin use data 588 or blood glucose monitor data 589, to determine the energy expenditure data 587. The energy expenditure data 587 is based both on the classified activity data 538, and on the insulin use data 588, blood glucose data 589 and the user data 526 from the health database 597. The classified activity data 538 may be communicated directly to a user at the communication module 542 or stored in the storage module 544, as classified activity data 538 alone or as part of the energy expenditure data 587, which may also be communicated directly to a user at the communication module 542 or stored in the storage module 544.

In addition to communicating the energy expenditure data 587 to a user through the communication module 542 and storing the energy expenditure data in the storage module 544, the energy expenditure data 587 is passed to an insulin requirement calculator 555 to define the insulin requirement data 592. The insulin requirement data 592 is passed to the insulin delivery module 594. Depending on criteria established for the subject, including the user data 526 from the health information database 597, and on the insulin requirement data 592, the system 510 may cause the insulin delivery module 594 to administer insulin to the subject, report the insulin requirement data 592 through the communication module 542 and record the insulin requirement data 592 in the storage module 544.

Figure 16:
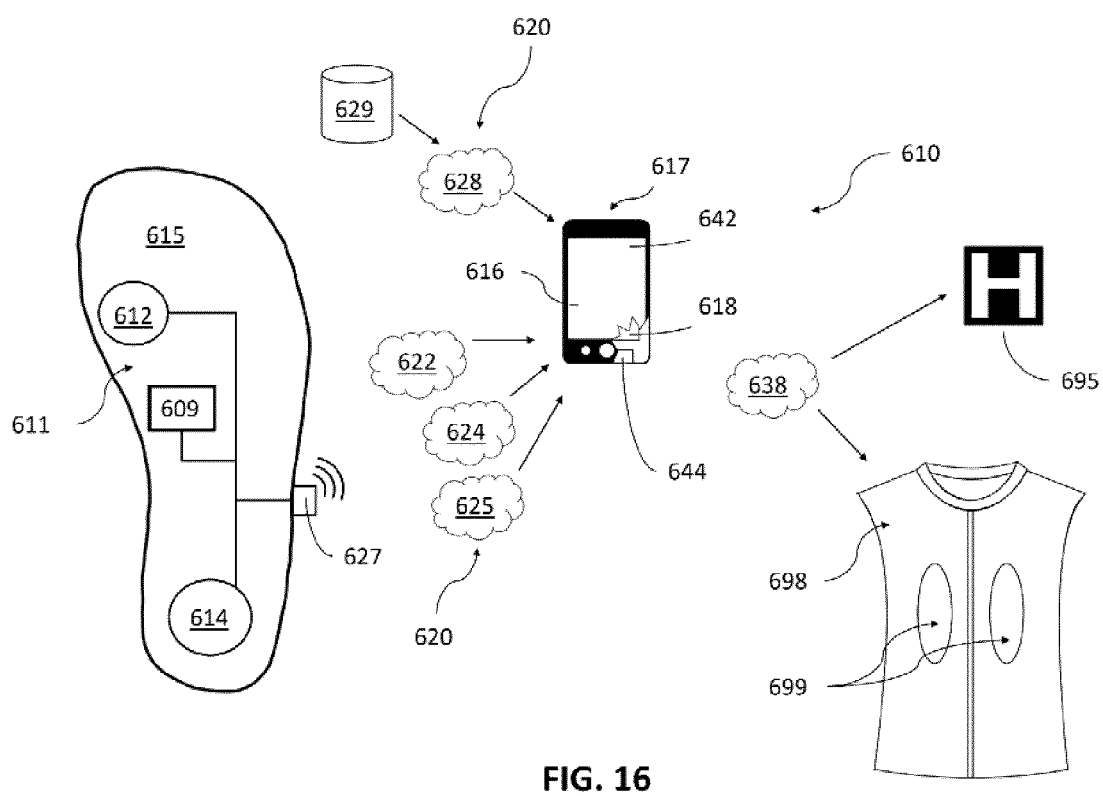
FIG. 16 is an activity classification system for fall prevention using a NN.

FIG. 16 shows a schematic of an activity classification system 610 for classifying the input data 620 resulting from activities performed by the subject for mitigating or preventing falls. The sensor module 611 and the training database 629 provide the input data 620. The input data 620 is processed by the processor 618 on the first device 617, which is shown as a smart phone. The sensor module 611 is located on the support matrix 615. The communication module 642 communicates the classified activity data 638 to a user of the system. The user may be the subject wearing the insole with the support matrix 615 or a different individual. The communication module 642 may also communicate the classified activity data 638 to the subject through an alert output 699, which may be located on a garment 698, in the event that the classified activity data 638 is indicative of an imminent fall. The communication module 642 may also communicate the classified activity data 638 to a health care provider 695 in the event that the classified activity data 638 is indicative of a fall. The classified activity data 638 may also be stored on the storage module 644.

The sensor module 611 includes the first pressure sensor 612, the second pressure sensor 614 and the other sensor 609 on the support matrix 615 for receiving the input data 620. The other sensor 609 may include any other sensor that measures a level of physical activity or other variable accounted for by the NN 690 (see FIG. 17). The first pressure sensor 612 generates the first pressure data 622. The second pressure sensor 614 generates the second pressure data 624. The other sensor 609, in this case an IMU receives the other sensor data 625, in this case shown as IMU data. The first pressure sensor 612, the second pressure sensor 614 and the other sensor 609 may be combined with additional sensors, as may be suitable for the application in respect of which the system 610 is applied. The first pressure sensor 612, the second pressure sensor 614 and the other sensor 609 may each be either binary sensors with a defined threshold for a positive reading, or may be sensors that detect a quantitative value.

The input data 620 may include the training data 628. The training data 628 may be accessed from the training database 629 through a wired connection, through a wireless connection, from a remote service, or by any suitable access method. The training data 628 is received by the processor 618 with the input data 620 and may be provided to the NN 690 to train the NN 690. The training data 628 may include empirical pressure or other data from a plurality of other subjects, including subjects having similar or different specific attributes compared with the current subject. The training data 628 may include synthetic data generated from empirical pressure or other data from a plurality of other subjects, including subjects having similar or different specific attributes compared with the current subject. The training data 628 may include simulated pressure or other data. The training data 628 may be used to update the weights and biases applied in the NN 690.

Figure 17:
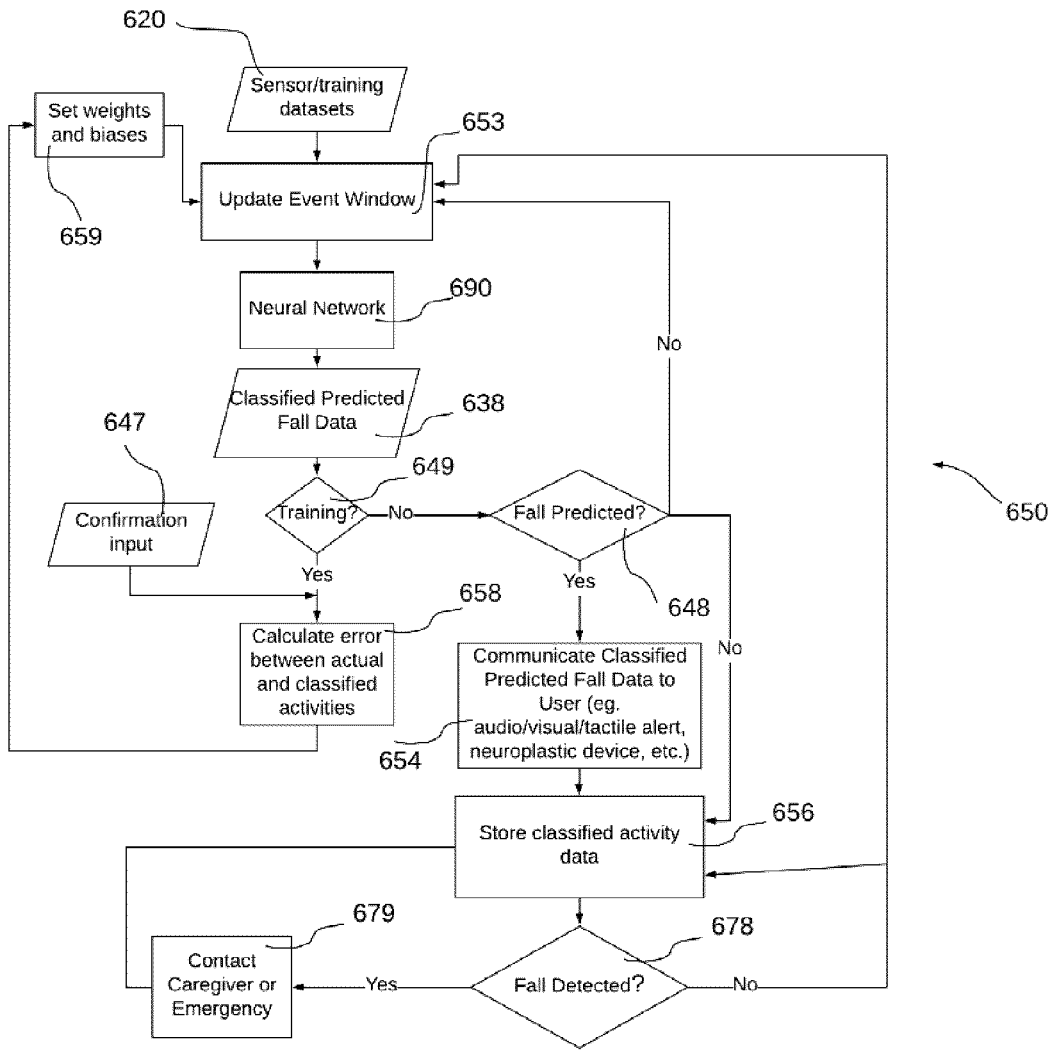
FIG. 17 is a flowchart of a method for classifying physical activities of a user with a NN and training the NN.

FIG. 17 is a flowchart of a method 650 for activity classification using the system 610. The method 650 includes updating an event window 653. An event window 675 (FIG. 18) is defined for the input data 620. The event window 675 is of a duration in time equal to an identified event from within the input data 620. The event may be identified by any suitable method, including by Fourier transform, adaptive filtering, or any suitable approach, including as described in WIPO (PCT) Patent Application No. CA2018/050802 to Cheng et al.

Depending on how the event is defined, the portions of the input data 620 within the event window 675 as it is progressed across a timeline of the input data 620 may overlap. Updating the event window 653 may include defining the event window 675 for the input data 620, changing the selection features for the event window 675 or progressing the event window 675 along the timeline of the input data 620 to the next identified event. The event window 675 may be applied only to a single type of event or may be applied to multiple distinct types of events. The events may be any event indicative of activities that the system 610 is being used to measure.

After updating the event window 653, the NN 690 is applied to a portion of the input data 620 within the event window 675, resulting in the classified activity data 638. Based on the classified activity data 638, where the fall prediction query 648 is negative, the method 650 will return to updating the event window 653. Based on the classified activity data 638, where the fall prediction query 648 is positive, the method 650 communicates the classified activity data to a user 654. An imminent fall alert may be communicated to the subject through a noticeable alert, such as an audio alarm, tactile stimulus or other output that is recognizable as urgent and simple to interpret, and providing the subject some warning that the system 610 has assessed a high likelihood of the subject falling. The method 650 may also include storing the classified activity data 656.

Where the system 610 is applying the training data 628 as the input data 620 and is training based on the resulting classified activity data 638 and the training confirmation 645, the loss function is calculated 658. The loss function is based on the difference between the classified activity data 638 of the training data 628 and the training confirmation 645. The loss function may be applied to setting weights and biases 659. After setting the weights and biases 659, additional input data 620 may be received and applied to the neural network 690.

Figure 18:
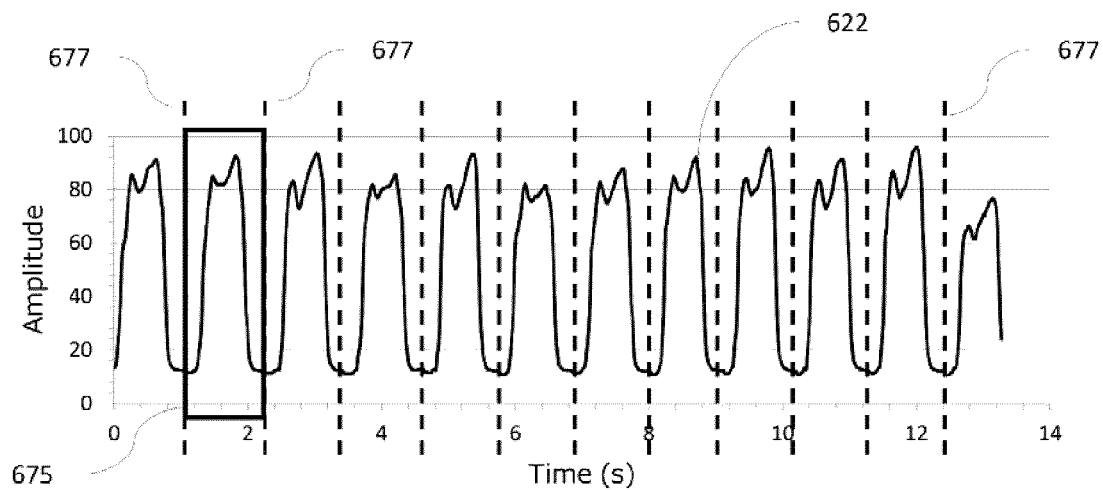
FIG. 18 is a schematic of example pressure data acquired with the system of FIG. 16 being processed with an event detection system.

FIG. 18 shows the input data 620 and the event window 675 superimposed over the input data 620 to defined a portion of the input data 620 to which the NN 690 will be applied to provide the classified activity data 638. The event window 675 is bounded by event limits 677 defined within the input data 620. The event limits 677 are defined when updating the event window 653.

The method and system may be used in sequence, with the output from a first activity classification NN used as input for a second activity classification NN. Multiple methods and systems of activity classification may be cascaded.

Figure 19:
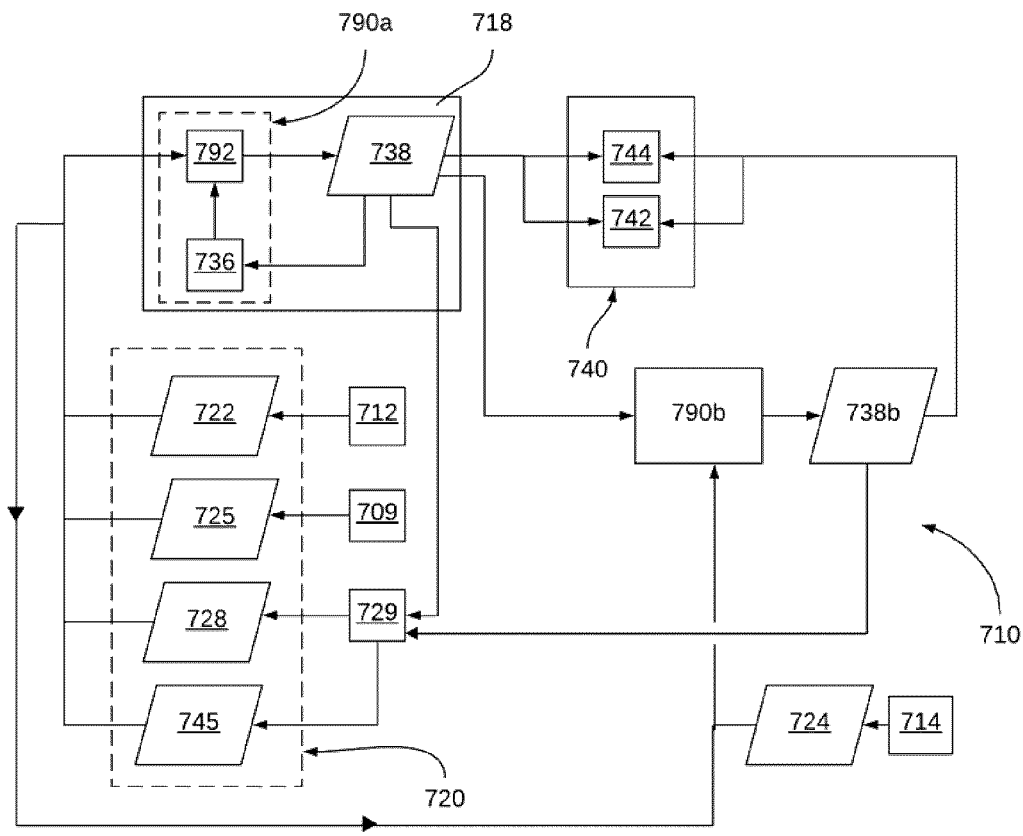
FIG. 19 is a schematic of a method using a first NN to provide classified activity data as input data to a second NN.

FIG. 19 shows a schematic of an activity classification system 710 for classifying the input data 720 including the pressure data 722a resulting from activities performed by the subject. The first pressure sensor 712a, the other sensor 709 and the training database 729 generate the input data 720. The input data 720 is communicated to the processor 718. The processor 718 applies the first NN 790a to the input data 720 for classifying the subject's activity and resulting in first classified activity data 738a that may be expressed in any suitable form. The input data 720 may also be applied to training the first NN 790a. The processor 718 communicates the first classified activity data 738a to the activity data module 740. The activity data module 740 may include the communication module 742 for communicating the first classified activity data 738a to a user or the storage module 744 for storing the first classified activity data 738a. The input data 720 may be provided to the processor 718 through a temporary storage module prior to any processing (e.g. a transitory local computer readable medium, a transitory cloud-based storage, etc.).

The sensors include the pressure sensor 712a and the other sensor 709 for receiving the input data 720. The other sensor 709 may include any suitable sensor that measures a level of physical activity. The pressure sensor 712a generates pressure data 722a. The other sensor 709 receives other sensor data 725. The pressure sensor 712a and the other sensor 709 may be combined with other sensors, as may be suitable for the application in respect of which the system 710 is applied. The pressure sensor 712a or the other sensor 709 may be either binary sensors with a defined threshold for a positive reading, or may be sensors that detect a quantitative value.

The input data 720 is received by the processor 718. The input data 720 may include the training data 728. The training data 728 may be accessed from the training database 729 accessed through a wired connection, through a wireless connection, from a remote service, or by any suitable access method. The training data 728 is received by the processor 718 with the input data 720 and may be provided to the first NN 790*a* to train the first NN 790*a*. The training data 728 may include empirical pressure or other data from a plurality of other subjects, including subjects having similar or different specific attributes compared with the current subject. The training data 728 may include synthetic data generated from empirical pressure or other data from a plurality of other subjects, including subjects having similar or different specific attributes compared with the current subject. The training data 728 may include simulated pressure data or other data. The first classified activity data 738*a* and the second classified activity data 738*b* may also be provided to the training database 729 for increasing the amount of training data 728 in the training database 729. The training data 728 and the training confirmation 745 may be applied to train the second NN 790*b*.

The training confirmation 745 may be received from the training database 729 by the processor 718 and applied to train the first NN 790*a* based on the first classified activity data 738*a* resulting from the training data 728 received from the training database 729. The training confirmation 745 may provide actual classified activity data for comparing with the first classified activity data 738*a* and training the first NN 790*a*. The training data 728 and the training confirmation 745 may also be applied to train the second NN 790*b*.

The first classified activity data 738*a* may be communicated to the activity data module 740 for feedback to be provided to the user through the communication module 742 based on the first classified activity data 738*a*. The activity data module 740 may allow for further processing and review of the first classified activity data 738*a* through the storage module 744. The first classified activity data 738*a* may be provided to the training database 729 for accessing in subsequent rounds of training and as part of the training data 728. In some cases, the training may be carried out with reference to the training data 728 as part of configuration or updating of the system 710, and some such systems may function without application of the subject training.

The first classified activity data 738*a* is also provided to a second NN 790*b*. The second NN 790*b* is applied to the first classified activity data 738*a* and the second pressure data 724. The second pressure sensor 714 receives the second pressure data 724 for providing to the second NN 790*b*. The activity data module 740 may include the communication module 742 for communicating the second classified activity data 738*b* to a user or the storage module 744 for storing the second classified activity data 738*b*. The second classified activity data 738*b* may also be provided to the training database 729 to supplement the training data 728. The first pressure data 722 and the other data 725 may also be provided to the second NN 790*b* for classification into the second classified activity data 738*b*.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method for classifying an activity of a subject comprising:
   receiving input data of the subject resulting from the activity, the input data including pressure data;
   applying a deep learning neural network to the input data based on weights and biases, resulting in classified activity data;
   training the deep learning neural network for updating the weights and biases; and
   communicating the classified activity data to a user.

2. The method of claim 1 wherein the input data further comprises data from an accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, or drug level sensor.

3. The method of claim 1 wherein the input data comprises separate sensors on a support matrix located to receive the input data from different portions of the subject; and the weights and biases are initially determined with reference to locations of the separate sensors on the support matrix.

4. The method of claim 1 wherein training the deep learning neural network comprises:
   confirming the activity, resulting in a defined activity and corresponding classified actual activity data;
   defining a loss function between the classified actual activity data and the classified activity data; and
   updating the weights and biases for mitigating the loss function; and
   wherein confirming the activity comprises on or many of the following operations:
   prompting the subject to perform the defined activity;
   receiving a confirmation input that the subject performed the defined activity;
   receiving the confirmation input from the subject; and
   receiving the confirmation input from an individual other than the subject.

5. The method of claim 1 wherein the deep learning neural network comprises a translationally invariant neural network,
the translationally invariant neural network comprising:
at least one convolutional layer; and
at least one fully connected layer subsequent to the at least one convolutional layer;
and wherein the fully connected layer comprises attribute data of the subject, the attribute data of the subject concatenated with the fully connected layer.

6. The method of claim 1 wherein training the deep learning neural network comprises receiving training data, the training data comprises synthetic input data generated from empirical input data.

7. The method of claim 6 wherein the synthetic input data is generated from the empirical input data by applying to the empirical input data one or many of the following operations: time-shifting, magnitude-scaling and spectral magnitude-scaling.

8. The method of claim 1 wherein communicating the classified activity data to the user comprises one or many of the following operations: displaying the classified activity data; providing tactile stimulus to the subject; and storing the classified activity in a database.

9. The method of claim 1 wherein the activity comprises activity indicative of an imminent fall and communicating the classified activity data to the user comprises a tactile or other neuroplastic stimulus to prompt the user to correct the activity and avoid a fall.

10. The method of claim 1 wherein the activity further comprises a fall and further comprising communicating the classified activity data of the fall to a third party.

11. The method of claim 1 further comprising applying a time window to the input data to provide time-segmented input data; and wherein applying the deep learning neural network to the input data comprises applying the deep learning neural network to the time-segmented input data.

12. The method of claim 11 further comprising weighting the time-segmented input data to provide weighted input data and wherein applying the deep learning neural network to the input data comprises applying the deep learning neural network to the weighted input data.

13. The method of claim 1 further comprising applying an event detection filter to the input data to provide event-classified input data; and wherein applying the deep learning neural network to the input data comprises applying the deep learning neural network to the event-classified input data.

14. A system for classifying activity of a subject comprising:
a sensor module comprising a pressure sensor, the sensor module for generating input data during the activity, the input data including pressure data;
a processor configured for receiving the input data, the processor configured for executing a method comprising:
applying a deep learning neural network to the input data based on weights and biases, resulting in classified activity data; and
training the neural network for updating the weights and biases.

15. The system of claim 14 wherein the sensor module comprises at least two pressure sensors; and the weights and biases are based on known relationships between the at least two pressure sensors.

16. The system of claim 14 wherein the sensor module further comprises an accelerometer, a gyroscope, a seismograph, a thermometer, or a humidity sensor, an altimeter, a GPS, a video camera, a heart rate sensor, an oxygen sensor, a breathing rate sensor, a blood glucose sensor, a fatigue measuring device, a limb position measuring device, a blood pressure monitor, an ECG, a lung function meter, an alcohol level sensor, drug level sensor, or any other type of sensor that measures a level of impairment.

17. The system of claim 14 wherein the deep learning neural network comprises a translationally invariant neural network; and
the neural network comprises:
at least one convolutional layer; and
at least one fully-connected layer subsequent to the at least one convolutional layer.

18. The system of claim 14 wherein applying a deep learning neural network to the input data comprises applying a time window to the input data to provide time-segmented input data; and applying the deep learning neural network to the time-segmented input data.

19. The system of claim 14 wherein applying a deep learning neural network to the input data comprises applying an event detection filter to the input data to provide event-classified input data; and applying the deep learning neural network to the event-classified input data.

20. The system of claim 14 wherein training the deep learning neural network comprises:
confirming the activity, resulting in a defined activity and corresponding classified actual activity data;
defining a loss function between the classified actual activity data and the classified activity data; and
updating the weights and biases for mitigating the loss function; and
wherein the training data comprises synthetic input data generated from empirical input data.

* * * * *